(12) United States Patent  
Dana et al.

(10) Patent No.: US 12,114,931 B2  
(45) Date of Patent: Oct. 15, 2024

(54) METHOD AND DEVICE FOR REMOTE OPTICAL MONITORING OF INTRAOCULAR PRESSURE

(71) Applicant: SmartLens, Inc., Mountain View, CA (US)

(72) Inventors: Aykutlu Dana, San Jose, CA (US); Sevda Agaoglu, Santa Clara, CA (US); Ahmet Taylan Yazici, Palo Alto, CA (US); Murat Baday, Palo Alto, CA (US); Savas Komban, Palo Alto, CA (US)

(73) Assignee: SmartLens, Inc., Mountain View, CA (US)

( * ) Notice: Subject to any disclaimer, the term of this patent is extended or adjusted under 35 U.S.C. 154(b) by 538 days.

(21) Appl. No.: 17/370,735

(22) Filed: Jul. 8, 2021

(65) Prior Publication Data

US 2021/0369111 A1    Dec. 2, 2021

Related U.S. Application Data

(63) Continuation of application No. PCT/US2020/013049, filed on Jan. 10, 2020.

(60) Provisional application No. 62/790,752, filed on Jan. 10, 2019.

(51) Int. Cl.
| | |
|---|---|
| *A61B 3/16* | (2006.01) |
| *A61M 35/00* | (2006.01) |
| *G02B 5/30* | (2006.01) |
| *G02C 7/02* | (2006.01) |
| *H04N 23/57* | (2023.01) |

(52) U.S. Cl.  
CPC ............... *A61B 3/16* (2013.01); *A61M 35/10* (2019.05); *G02B 5/30* (2013.01); *G02C 7/02* (2013.01); *H04N 23/57* (2023.01)

(58) Field of Classification Search  
CPC ......... A61B 3/16; A61B 3/0025; A61B 3/107; A61M 35/10; G02B 5/30; G02C 7/02; G02C 11/04; G02C 11/10; H04N 23/57  
See application file for complete search history.

(56) References Cited

U.S. PATENT DOCUMENTS

| | | |
|---|---|---|
| 5,840,041 A | 11/1998 | Petter et al. |
| 7,981,097 B2 | 7/2011 | Paoli, Jr. |
| 10,016,132 B2 | 7/2018 | Mandel et al. |
| 10,085,637 B2 | 10/2018 | Araci et al. |
| 10,219,696 B2 | 3/2019 | Araci et al. |

(Continued)

FOREIGN PATENT DOCUMENTS

| | | |
|---|---|---|
| AU | 2017201863 A1 | 4/2017 |
| WO | WO-9620635 A1 | 7/1996 |

(Continued)

OTHER PUBLICATIONS

EP20738775.4 Extended Search Report dated Sep. 6, 2022.

(Continued)

*Primary Examiner* — James C. Jones  
(74) *Attorney, Agent, or Firm* — Wilson Sonsini Goodrich & Rosati

(57) ABSTRACT

A wearable eyewear device, methods of use and systems are described that allow a person wearing the eyewear device to accurately measure the intraocular pressure of their eye, and dispense a medication to the eye when needed.

17 Claims, 22 Drawing Sheets

(56) References Cited

U.S. PATENT DOCUMENTS

| | | | |
|---|---|---|---|
| 10,898,074 B2 | 1/2021 | Araci et al. | |
| 11,213,203 B2 | 1/2022 | Mandel et al. | |
| 11,759,107 B2 | 9/2023 | Araci et al. | |
| 2009/0076367 A1 | 3/2009 | Sit et al. | |
| 2010/0016704 A1 | 1/2010 | Naber et al. | |
| 2013/0184554 A1 | 7/2013 | Elsheikh et al. | |
| 2013/0253451 A1 | 9/2013 | Kim | |
| 2013/0278887 A1 | 10/2013 | Legerton | |
| 2014/0243645 A1 | 8/2014 | Leonardi | |
| 2014/0354942 A1 | 12/2014 | Pugh et al. | |
| 2016/0015265 A1 | 1/2016 | Mandel et al. | |
| 2016/0270656 A1 | 9/2016 | Samec et al. | |
| 2017/0000341 A1* | 1/2017 | Samec | A61B 3/113 |
| 2017/0165439 A1 | 6/2017 | Kaufmann | |
| 2018/0279870 A1 | 10/2018 | Walsh et al. | |
| 2018/0296390 A1 | 10/2018 | Hoare | |
| 2020/0138669 A1 | 5/2020 | Berdahl et al. | |
| 2021/0298677 A1 | 9/2021 | Dana et al. | |
| 2022/0022744 A1 | 1/2022 | Dana et al. | |
| 2022/0361751 A1 | 11/2022 | Dana et al. | |
| 2023/0380686 A1 | 11/2023 | Araci et al. | |
| 2023/0381017 A1 | 11/2023 | Dana et al. | |

FOREIGN PATENT DOCUMENTS

| | | |
|---|---|---|
| WO | WO-2007136993 A1 | 11/2007 |
| WO | WO-2014137840 A1 | 9/2014 |
| WO | WO-2018221687 A1 | 12/2018 |
| WO | WO-2019175667 A1 | 9/2019 |
| WO | WO-2020060558 A1 | 3/2020 |
| WO | WO-2020124074 A1 | 6/2020 |
| WO | WO-2020146714 A1 | 7/2020 |
| WO | WO-2021154729 A1 | 8/2021 |
| WO | WO-2022182629 A1 | 9/2022 |

OTHER PUBLICATIONS

Agaouglu et al. Ultra-sensitive microfluidic wearable strain sensor for intraocular pressure monitoring. Lab on a Chip, Issue 22, 2018; pp. 3471-3483.

PCT/US2020/013049 International Search Report and Written Opinion of the International Searching Authority dated Mar. 19, 2020.

Co-pending U.S. Appl. No. 18/500,766, inventors Araci; Ismail Emre et al., filed Nov. 2, 2023.

EP21748263.7 Extended European Search Report dated Oct. 9, 2023.

PCT/US2021/015093 International Search Report & Written Opinion of the International Searching Authority dated Jun. 3, 2021.

PCT/US2022/017224 International Search Report and Written Opinion dated May 11, 2022.

* cited by examiner

Laser spots from hologram falling on cornea from the side

- For given Cornea geometry
  - For given Camera set and lightsource set geometry
    - For each Cornea coordinate $\{X_c, Y_c, Z_c, \theta_c\}$
      - For each Cornea Radius r
        - For each light source s
          - For each camera k
            - Generate ray tracing model based on $\{X_c, Y_c, Z_c, \theta_c\}$ and r
            - Calculate peak position in ray trace images $(X_{c,r,s,k}, Y_{c,r,s,k})$ and peak width $W_{c,r,s,k}$
            - Generate Training vectors $T=\{s,k, x_{c,r,s,k}, Y_{c,r,s,k}, W_{c,r,s,k}\}$, $O=\{X_c, Y_c, Z_c, \theta_c, r\}$
- Use training vectors $T=\{s,k, x_{c,r,s,k}, Y_{c,r,s,k}, W_{c,r,s,k}\}$ as input and $O=\{X_c, Y_c, Z_c, \theta_c, r\}$ as desired output, to train the neural network

FIG. 19

METHOD AND DEVICE FOR REMOTE OPTICAL MONITORING OF INTRAOCULAR PRESSURE

CROSS-REFERENCE TO RELATED APPLICATIONS

This application is a continuation of PCT Application No. PCT/US20/13049, filed Jan. 10, 2020, which claims priority from U.S. Provisional Application 62/790,752 entitled "Method and Device for Remote Optical Monitoring of Intraocular Pressure," filed Jan. 10, 2019, the contents of which are hereby incorporated by reference in their entirety.

BACKGROUND

Field

The present disclosure is related to a system and methods of using a wearable optical imaging sensor system for measuring intraocular pressure.

Background

Glaucoma is the second most common cause of blindness in the global world. It is a multifactorial disease with several risk factors, of which intraocular pressure (IOP) is the most important. IOP measurements are used for glaucoma diagnosis and patient monitoring. IOP has wide diurnal fluctuation, and is dependent on body posture, so the occasional measurements done by the eye care expert in a clinic can be misleading.

Previously (US20160015265A1, 2018), an implantable microfluidic device has been proposed for intraocular pressure monitoring, that can be used for glaucoma diagnosis. Later, a wearable device was demonstrated (Lab Chip, 2018, 18, 3471-3483) to serve the same purpose, however without needing implantation. In these previous studies, it was established that intraocular pressure increases results in bulging of the cornea and consequently changes in the radius of curvature.

In literature, it is shown that the IOP changes affect the corneal topography, causing changes in corneal radius and apex height with respect to the corneal periphery. If the corneal topography can be measured accurately, the 4 micrometer change in corneal radius per 1 mmHg IOP change can be monitored and IOP value can be inferred.

Thus there remains a need for an IOP measuring device that can take multiple measurements of a patient eye throughout the day as the patient goes through their normal routine.

There is also a need for a device that has sufficient sensitivity to take measurements to produce reliable data for accurate diagnosis.

There is still further a need for such a device to operate in a manner that does not interfere with a patient's normal vision and activities.

There is still further a need for a device that can operate reliably while a patient carries on their normal daily activities, and the device does not require a particular critical position or alignment relative to the patient's eyes. The device should be user friendly.

BRIEF SUMMARY

These and other objectives may be met using the device, system and methods described herein. In various embodiments, the present disclosure relates to a wearable optical device (such as eyewear, goggles or visors) for measuring the intraocular pressure of an eye.

In an embodiment, there may be an eyewear device for measuring intraocular pressure (IOP). The device may have a frame, a first lens mounted to the frame such that the lens may be in the field of view of a person wearing the eyewear device. The eyewear device may have a first illumination source positioned to illuminate the eye of a user, a first image sensor positioned to capture images of the eye of the user, a first communication portal being in electronic or signal communication with a computational device and a first drug dispensing device being aligned to deliver a dose of a drug to the eye of the user.

In another embodiment there may be a method of training an image processing pipeline. The method involves collecting personalized ophthalmologic data on a user's anatomy and a user's corneal properties at a known IOP, collecting personalized data from an eyewear device for measuring IOP, and using at least one computational mode and ray tracing under one or more geometric configurations to generate at least one set of training data for a neural network components pipeline.

In another embodiment there may be a system for measuring and treating the IOP of a patient. The system may have: a computational device, a wearable eyewear device for collecting IOP data and being in signal communication with the computational device, the eyewear device having a drug dispensing component. The system may also have a database containing a user profile including personalized ophthalmologic reference data where the database may be accessed by the computational device, and where the database, and the IOP data are used to determine a treatment regimen for a user's eye. A drug delivery component on the eyewear may deliver the drug in response to a signal from the computational device.

In various embodiments, the computational device may be a cell phone, a tablet or a laptop computer. In still other embodiments, the computational device may be attached to the wearable eyewear device.

Devices, systems and methods are described herein using eyewear with one or more illuminators and one or more image sensors. The combination of illuminator(s) and image sensor(s) may operate to eliminate one or more of ambient lighting changes and/or misalignment error, while providing a sensitive and accurate measurement of the cornea radius. A small change of the radius of curvature (as small as 4 micrometers per 1 mmHg change in IOP) may be observed for a typical adult cornea. The optical design may allow image processing and sensor fusion, as well as machine learning to accurately and sensitively measure the radius of curvature changes in the cornea. The measured changes may be used in a calculation using a machine learning program, a learning neural network, an artificial intelligence program, or other analytic computational program to relate the measured changes in radius to the IOP. The method may use a preliminary characterization of the corneal thickness and topography where the radius of curvature at a known IOP reading is acquired by conventional ophthalmologic methods. The personalized data set may then use as an input into the data processing algorithms, that also use continuous imaging measurements from the eyewear to calculate the IOP. The data may be connected to a computational device such as a cell phone or the cloud, and the eyewear may dispense a drug using a drug dispensing device. The drug may help reduce the IOP of the eye. The present disclosure includes a wearable optical device that measures the IOP through image acquisition from one or more image sensors, and uses the image data along with a reference data for a particular individual to accurately determine the IOP, and may dispense drugs to the eye to control the IOP.

BRIEF DESCRIPTION OF THE SEVERAL VIEWS OF THE DRAWINGS

Reference is now made to the drawings in brief, where like part numbers refer to the same part. Otherwise different part numbers, even if similar to other part numbers, represent different parts of different embodiments. Elements in the illustrations are not shown to scale unless specifically indicated, and may be distorted to some degree to emphasize the element or some characteristic of the element. Not all parts are shown in all embodiments so that the view of the figure does not become unnecessarily distorted.

FIG. 19 illustrates a sample logic according to an embodiment.

DETAILED DESCRIPTION

Figure 1:
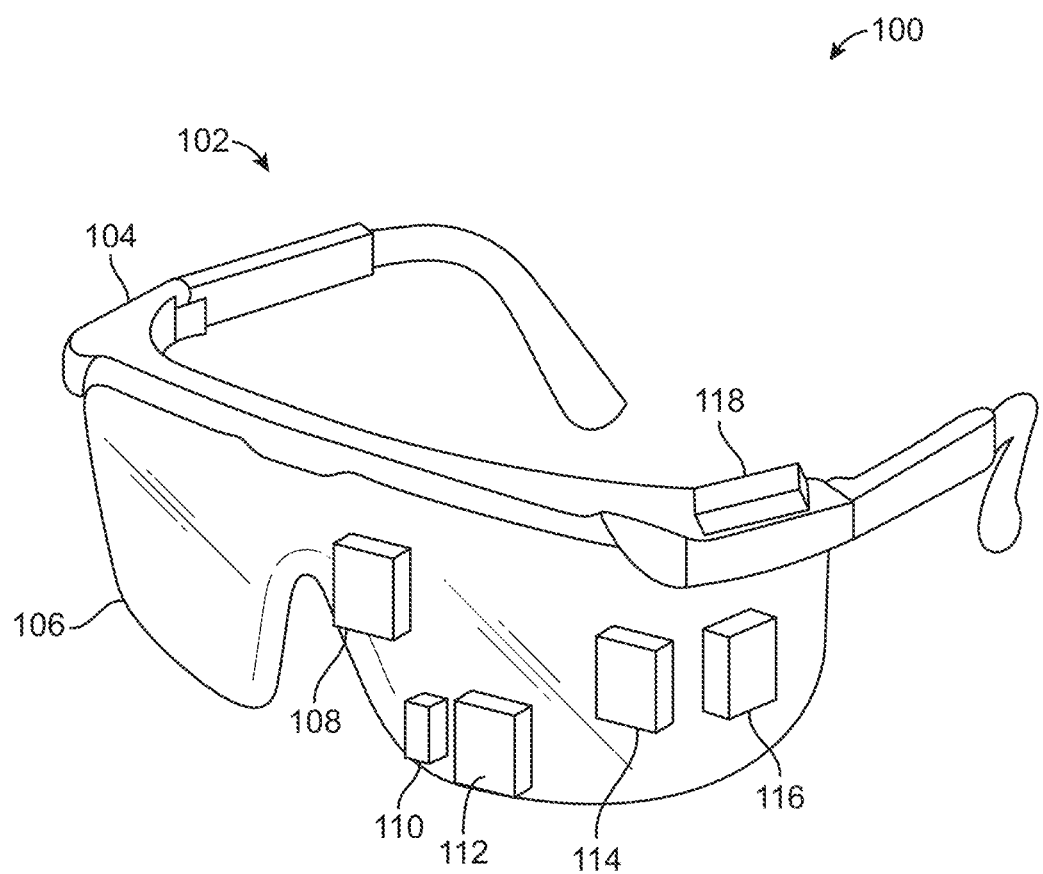
FIG. 1 illustrates an optical imaging sensor goggle for measuring the intraocular pressure remotely (IOP goggle) according to an embodiment.

The present disclosure describes wearable eyewear, systems and methods for measuring the cornea of an eye, and determining the intraocular pressure of the measured eye based on the curvature of the cornea. The disclosure includes eyewear, a computational device for calculating IOP values based on cornea data collected by the eyewear, and methods for calculating the IOP, and dispensing a drug to the eye when needed.

The eyewear as described herein may take a variety of forms. The form factor may be one of choice for a user, or one for the user's optometrist or other professional medical person responsible for the user's eye health. In some embodiments, the form factor may include a frame and a lens. The frame may be one where the user may wear in front of his eyes (note the use of male or female pronouns may be distributed herein randomly. The disclosed technology is not dependent on the gender of the user. The interchanging use of the gender of the user or other persons described herein is simply for the convenience of the applicant). The frame may be any sort of eyewear frame used for modern eyewear, including frames for sun glasses, vision correction glasses, safety glasses, goggles of all types (e.g. Swimming, athletic, safety, skiing, and so on). The frame may be suitable for a single lens for one eye, a lens for two eyes (e.g. a visor), or a single lens and an eye cover (such as for persons with "lazy eye" or who may suffer from the loss of one eye). The lens may be a prescription lens for vision correction, a clear or tinted lens for appearance, or an opaque lens that covers the eye. In many embodiments, the lens may have a defined area for the field of view of the user. The field of few may be clear to avoid blocking the vision of the user. The various elements of the eyewear device may be place on the periphery of the lens, or on the frame. The frame or lens may have flanges or other protrusions or tabs for the attachment of image sensors, light sources, battery, computational devices, drug delivery devices, or any other component suitable for the use with the present disclosure.

The wearable eyewear may have one or more image sensors positioned to face the eye(s) of the user so the image sensor may capture an image of the eye. The image sensor may be a camera, a CCD (charge coupled device), CMOS (complementary metal oxide semiconductor), or other image capture technology. The wearable eyewear may have one or more light sources for projecting light at the eye. In some embodiments, the light source may be a form of illumination that produces specific wavelengths of light. The light emission may be at a shallow angle to the curvature of the cornea, and projected outside the lens portion of the eye so that the light does not interfere with the users normal vision. In some embodiments the light source may be a laser. In some embodiments the light source may be a LED (light emitting diode), and in other embodiments the light source may be any light generating technology now known or still to be developed.

In various embodiments, the light source(s) and image sensor(s) may be positioned so that images captured by the image sensor are able to ignore ambient light, glare or other optical artifacts that might interfere with the accurate reading of the change in cornea curvature. The light source and the image sensor may use one or more polarizing filters to substantially reduce or eliminate light of a particular polarization, wavelength or intensity, so the captured image may have greater reliability and less signal noise. In another embodiment the eyewear may have a light sensor to help regulate when the ambient lighting conditions are appropriate for taking a suitable image of the eye to determine the cornea curvature. The images captured by the image sensors may be stored locally for a period of time, or transmitted to a computational device via a communication portal.

In some embodiments, the communication portal may be an antenna for wireless transmission of data to a computational device. The communication portal may send and receive information, such as sending image data, and receiving dosing information for a drug delivery device. In various embodiments, the computational device may be a cell phone, a tablet computer, a laptop computer, or any other computational device a user may select to carry out program (App) functions for the eyewear device. In some embodiments, the computational device may be resident on the eyewear. In some embodiments, the communication portal may be a wired connection between the image sensors, the light sources, the computational device, and a power supply for all the electrical components. In still other embodiments, the communication portal may connect the eyewear to the cloud.

In an embodiment, there is a method for determining the IOP of an eye. In some embodiments, the method may use a basic operation pipeline. The pipeline may receive image data from a variety of sources. In some embodiments the image data may come from the eyewear as it is worn by a user. In some embodiments the image data may come from a database having stored ophthalmologic data of the user at a fixed point in time. In some embodiments the images may be anatomic data of a user from a fixed point in time. In an embodiment, some or all the available image data may be used in a deep neural network with an image processing front-end. The image processing front-end may derive or calculate an IOP reading. In some embodiments, the IOP reading may be updated at video data rates, providing a quasi-real time output.

In another embodiment, the data pipeline may cause an image sensor to change exposure levels, gain, brightness and contrast in order to capture non-saturated images. The images may be passed through a threshold filter to reduce or eliminate background noise. Some high resolution images may be stored in a temporary memory for rapid processing, while blurry and low resolution images are formed. The low resolution images may then be passed through a match filter or feature detection filter to pinpoint spots corresponding to particular illumination/light sources in the various captured images. The coarse locations may then be used to segment the high resolution images and perform peak fitting algorithms to individually determine the positions and widths of each peak in the images. The results of the peak locations and widths may then be used with the previously trained neural network, which may then be used to estimate cornea coordinate and radius of curvature. A nonlinear equation solver may be used to convert the radius of curvature into an IOP reading.

In an embodiment, the IOP reading may then be used to determine a drug dose to administer to the eye being monitored. The drug dose information may be relayed back through the communication portal to the eyewear and the drug dispensing device. The drug dispensing device may then administer the proper does to the eye. In some embodiments, the drug delivery device may use an atomizer. In other embodiments the drug delivery device may use eye drops. In still other embodiments, the computational device may provide an alert to the user to self administer a drug of a certain dose at a certain time.

As described herein, a wearable eyewear device may be coupled to a computational device to measure the IOP of a user's eye. The user may be a person wearing the eyewear unless the context of the usage clearly indicates otherwise.

Various aspects, embodiments and examples are described that may be imprecise. In medical technology and treatment, diagnosis, drug prescription and usage, as well as therapy regimens may not be the same for every person do to nuances in individual biology. Thus various embodiments described herein may use a term such as "generally," or "substantially." These terms should be understood to mean that due to variations of people, and variations of eyes, from each other, and from one person to the next, there may necessarily be variations in how some embodiments operate in calculations, in communications, in data manipulation and in treatment. We refer to "generally" and "substantially" as including any variation that fits the spirit of the present disclosure.

Reference is made herein to various components and images. The use of the references are to help guide the reader in a further understanding of the present disclosure. In particular, while the singular version of a noun is often used, it should be understood that the embodiments fully consider plural numbers of components and images to also be within the scope of the disclosure.

Referring now to the FIG. 1, an eyewear 102 device having a frame 104 and a lens 106 may be provided. The lens 106 may have a first light source 108, and one or more image sensor 112, 114 and 116 placed on it. In other embodiments, any one of the light source 108 or image sensors may be placed on the frame 104. In some embodiments the image sensors and light source 108 may be placed on either the frame 104, the lens 106, or partially on both. The eyewear 102 may also have a drug delivery device 110 positioned to deliver a medication directly to the eye. The drug delivery device 110 may be an atomizer or other aerosol device, a dropper or any other device for delivering mediation to the eye. In some embodiments, the drug delivery device 110 may be a mist applicator. In some embodiments, the mist applicator may be a MEMS (micro-electro-mechanical systems) atomizer with a cartridge for the dispensed drug, that may be replaced when needed. A controller 118 may control the individual image sensors, the light source 108 and the drug delivery device 110. The controller 118 may be connected to the other components via a wire or cable connection, or by using a short range wireless communication protocol to each. In some embodiments, each component may have its own power source. In some embodiments, a single power source may be wired to each of the components to power all the components as needed. In some embodiments, a combination of power sources, local and central, may be used.

In various embodiments, the power supply to the controller and other components may be replaceable. In some embodiments, there may be a drug reservoir (not shown) associated with the drug delivery device 110, and the drug reservoir may be replaceable, or refillable. In the drawing, the components are depicted as large blocks for illustration purposes only. The components are not to scale on the eyewear 102 and no interpretation of the size of the components should be assigned to them based on the drawing figure. The drawing figures are for illustration purposes only.

Figure 2:
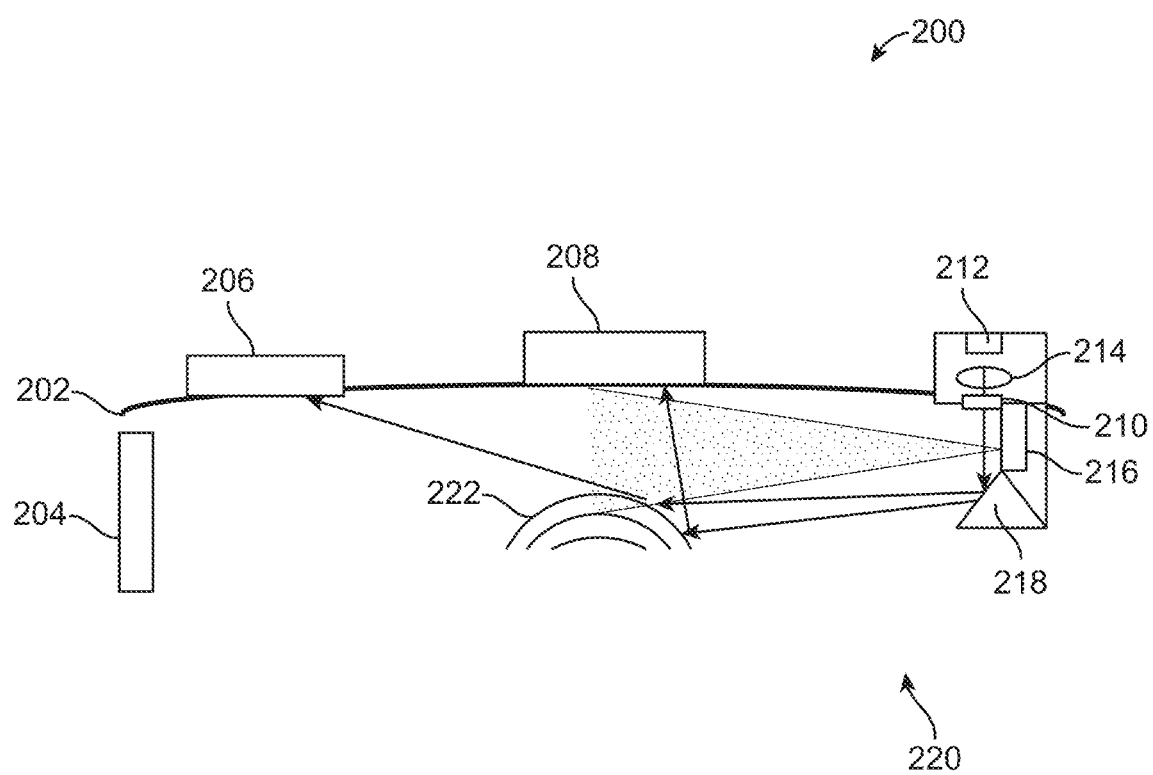
FIG. 2 illustrates a top view of an IOP goggle according to an embodiment.

In an embodiment, there may be an optical design for the eyewear 202 as shown in FIG. 2. The eyewear 202 may be fitted with a side illuminator made up of a planar illuminator 216, a laser diode 212 collimated by a collimator lens 214 and multiplied into a pattern by a hologram 210. The assembly of the planar illuminator 216, laser diode 212 and collimator lens 214 may make up a light source 220. The hologram 210 may be relayed towards the cornea 222 by a mirror 218. The reflections of the hologram 210 off the cornea 222 may be captured by one or more image sensor 204, 206, 208. In an embodiment, the planar illuminator 216 may provide wide angle and uniform illumination, allowing the image sensors to acquire images of the eye. The planar illuminator 216 may be turned on to acquire a background image of the cornea, pupil, and iris. It may then be turned off to allow background free image collection from other light sources such a laser diode 212, or any other light source that may be provided.

In an embodiment, the laser diode 212 may project a laser beam through the collimator lens 214 and through a hologram 210. The hologram 210 image reflects off the mirror 218 and shines on to the cornea 222. Depending on the curvature of the eye, the hologram image reflects to a first image sensor 208 and a second image sensor 206 as shown by the arrows. In this embodiment, the side image sensor 204 does not capture any image from the hologram reflection of the cornea 222.

Figure 3:
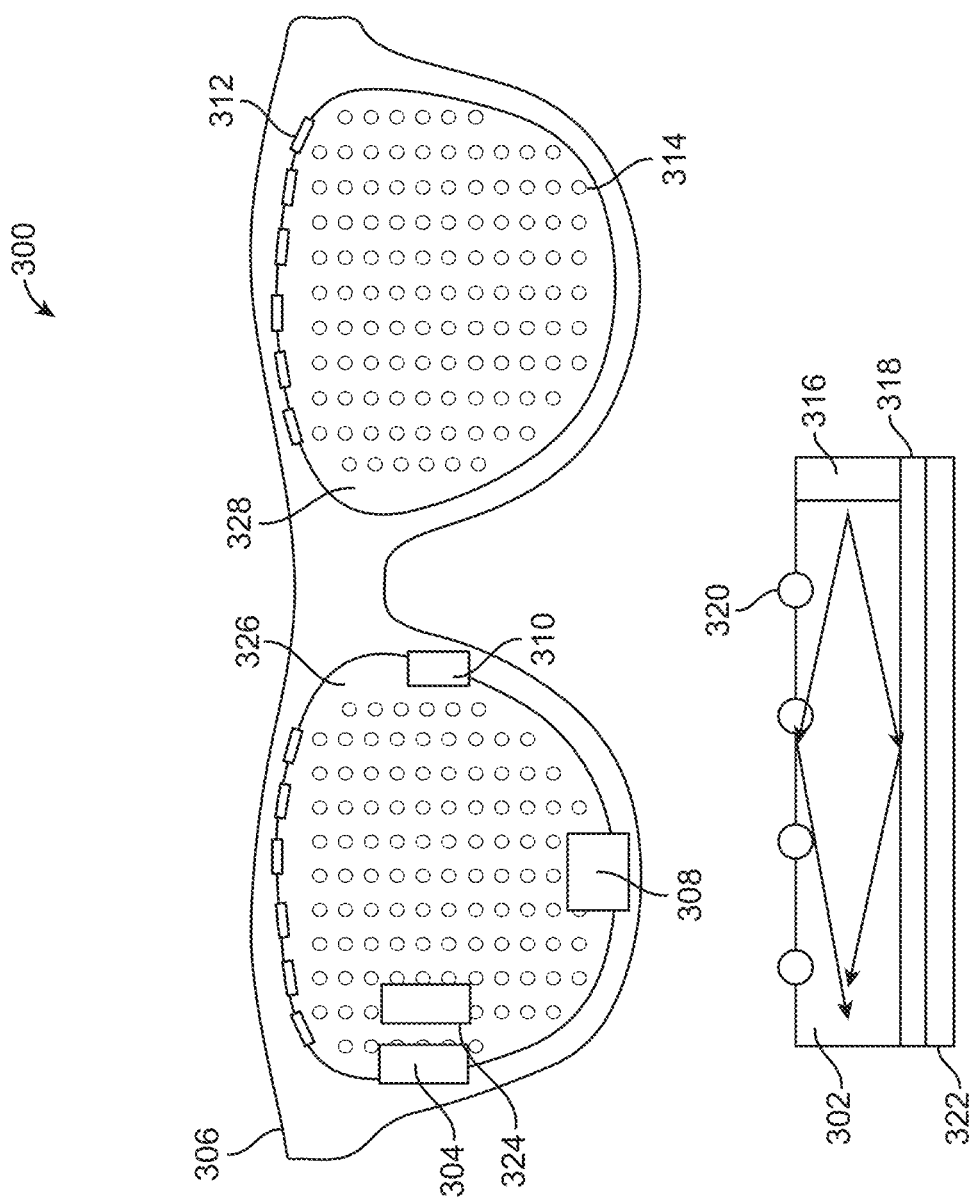
FIG. 3 illustrates a goggle according to an embodiment.

In an embodiment, an eyewear 302 device may be provided as shown in FIG. 3. In an embodiment, the eyewear 302 device may have a frame 306 holding a first lens 326 and a second lens 328. Image sensor 304, 308, 324 may be attached to the inside (facing the eye) of the lenses or the frame. A light source 310 may be positioned near the nose bridge of the eyewear frame 306.

In an embodiment, a cross section of a lens 326, 328 is shown. The eyewear lens has an array of spherical defects, which may also be sparsely positioned illuminators 320. A side illuminator 316 may project line into the lens. A low refractive index cladding layer 318 and a linear polarization film 322 form the front layer of the lens. The light from the side illuminator 316 travels through the lens.

In operation, the eyewear according to an embodiment may be fitted with planar side illuminator 312, 316, as well as an array of sparsely positioned illuminators 320 that may be embedded into the front cover of the lens of the eyewear 302. A linear polarization film 322 may allow one (vertical, horizontal or other planar orientation) polarization from the ambient light into the eyewear 302 to facilitate vision while blocking the other polarization. This relationship may help the eyewear to work without interference of any ambient light at the linear polarization film 322. A front image sensor 308, secondary image sensor 324 and a sideview image sensor 304 may have a crossed polarizer that may block the ambient light admitted by the linear polarization film 322. A drug delivery device may be incorporated into the eyewear to dispense drugs for IOP control based on the IOP readings. A waveguide approach to generating a see-through illumination pattern may be seen in the diamond shaped arrows in the cross section image of the lens. The windows of the eyewear have an array of spherical defect 314 and may be illuminated by a side illuminator 316 from within the lens. The lens maybe be coated with a low refractive index cladding layer 318 to separate the waveguide from the linear polarization film 322.

Figure 4:
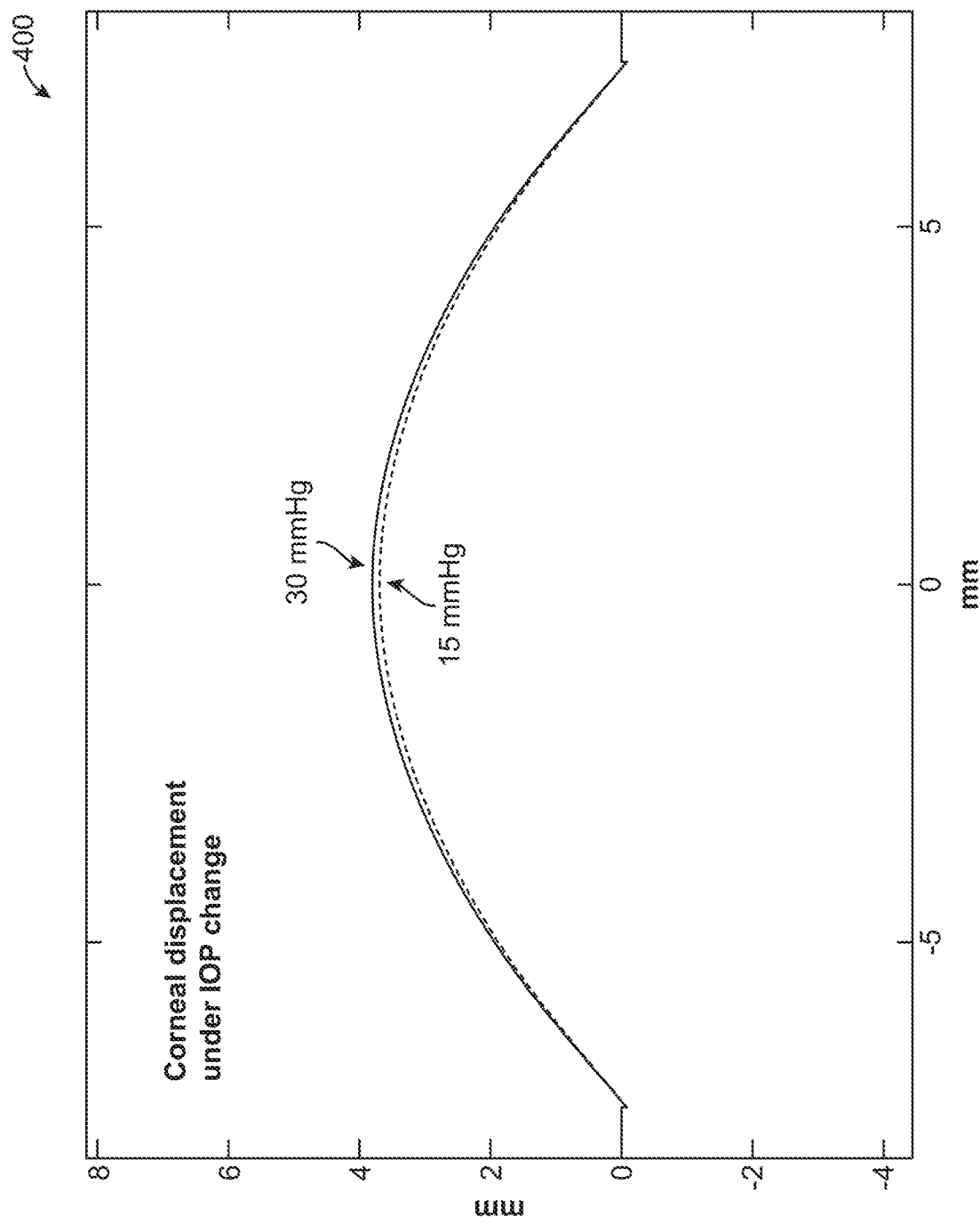
FIG. 4 illustrates the change in corneal topography when the IOP changes from 15 to 30 mmHg according to an embodiment.

An illustration of the cross section of corneal deflection is shown in FIG. 4. The illustration shows two curves, one raised slightly above the other. The top curve illustrates the corneal displacement of 30 mm Hg (30 mm of mercury pressure) and the bottom curve shows the corneal displacement for half that pressure, or 15 mm HG. The illustration provides two examples where the radius and the apex of the cornea may change due to IOP within the eye.

Figure 5:
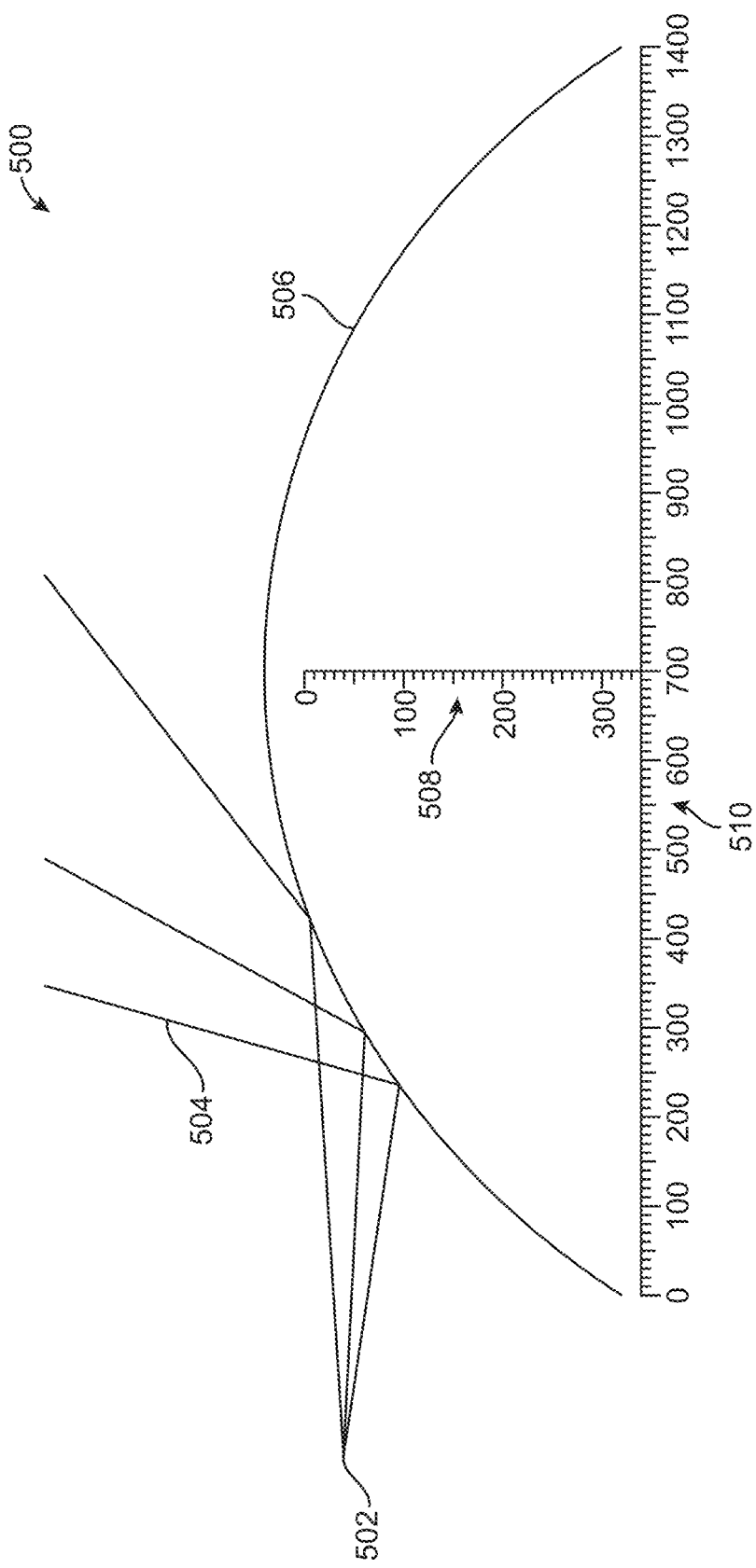
FIG. 5 illustrates a schematic ray trace showing optical beams bouncing off a cornea according to an embodiment.
Figure 6:
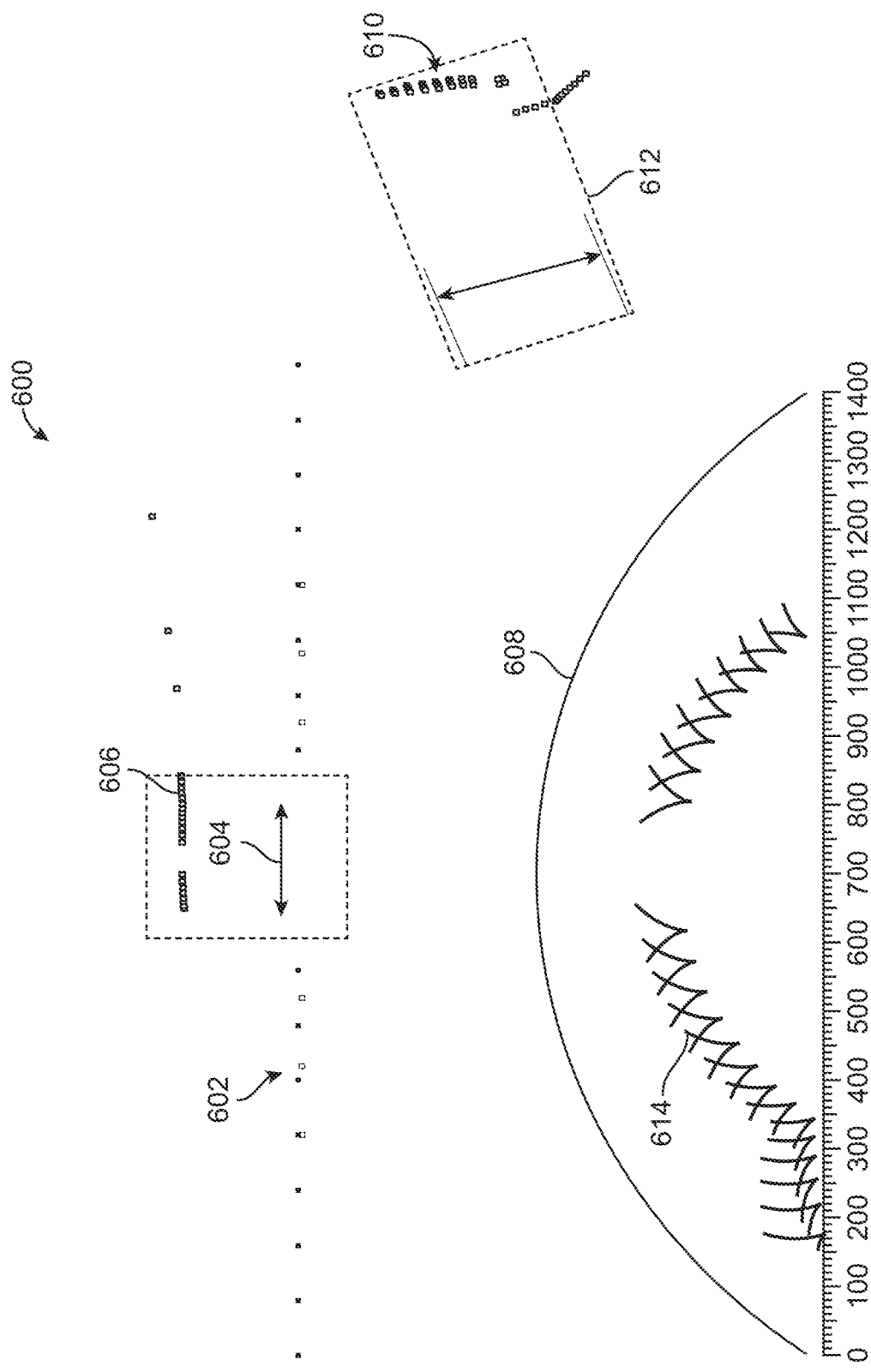
FIG. 6 illustrates a schematic ray trace showing optical beams forming images according to an embodiment.

An example of a ray trace diagram is now shown in FIG. 5. In an embodiment, a point source 502 may project light on to the surface of the cornea 506. The light rays may be reflected off the cornea 506 and form one or more reflection 504. The curvature of the cornea 506 as well as the angle of incidence and angle of reflection may be determined using the known position of the point source 502 relative to the cornea, the known angle of image capture by one or more image sensors, and the dispersion of the light from the point source as seen in the images captured. The y-axis 508 and x-axis 510 are provided for reference.

In an embodiment, an example ray trace from multiple point source 602 lighting may be arranged around the cornea 608. The light from each of the many point source 602 lighting may be captured at image sensor 604 and image sensor 612, producing real image 606 and real image 610 respectively. Virtual images 614 may also be conceptualized.

Figure 7:
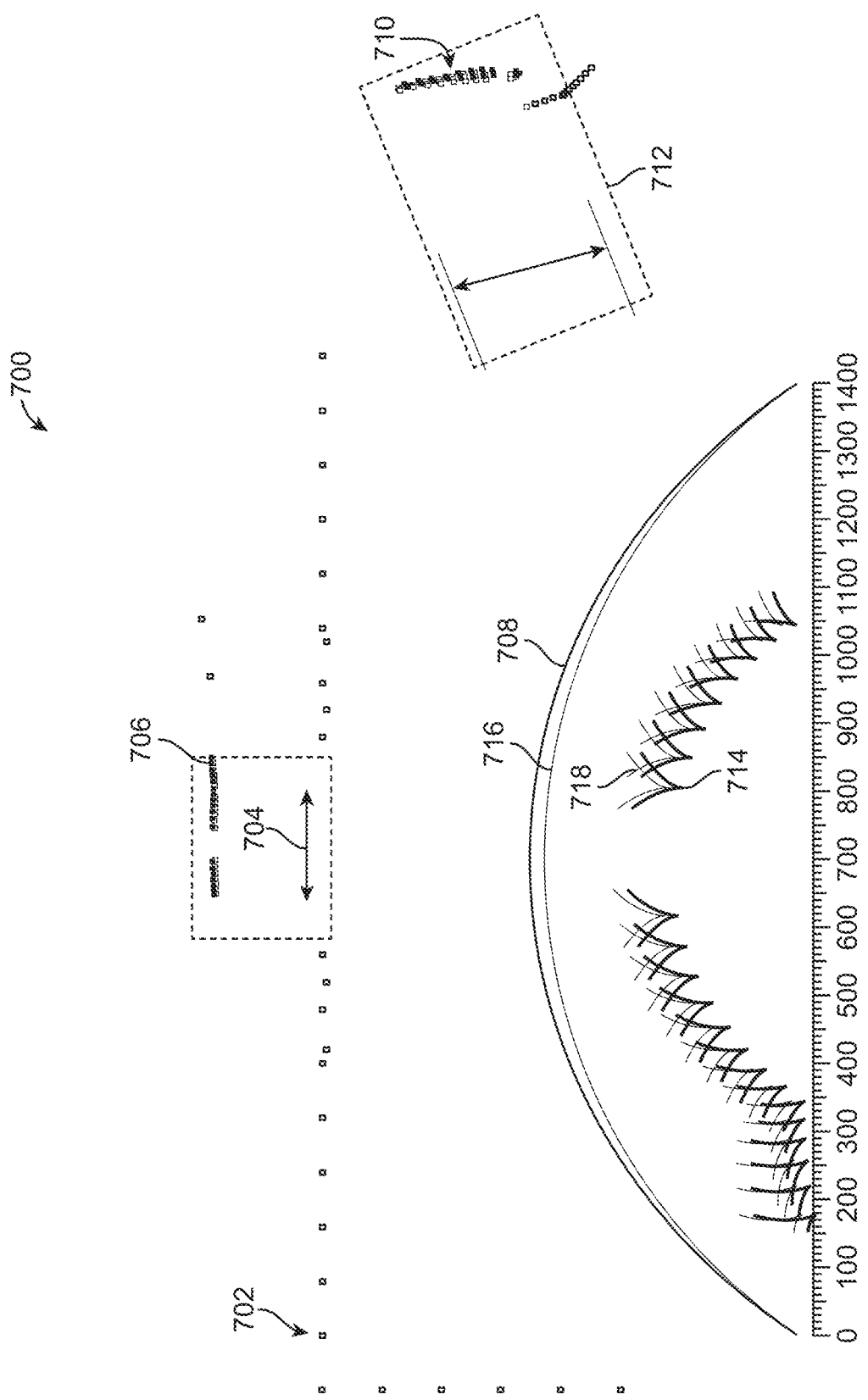
FIG. 7 illustrates a schematic ray trace that shows images of the point-sources at the camera's image planes when the corneal Radius changes according to an embodiment.
Figure 8:
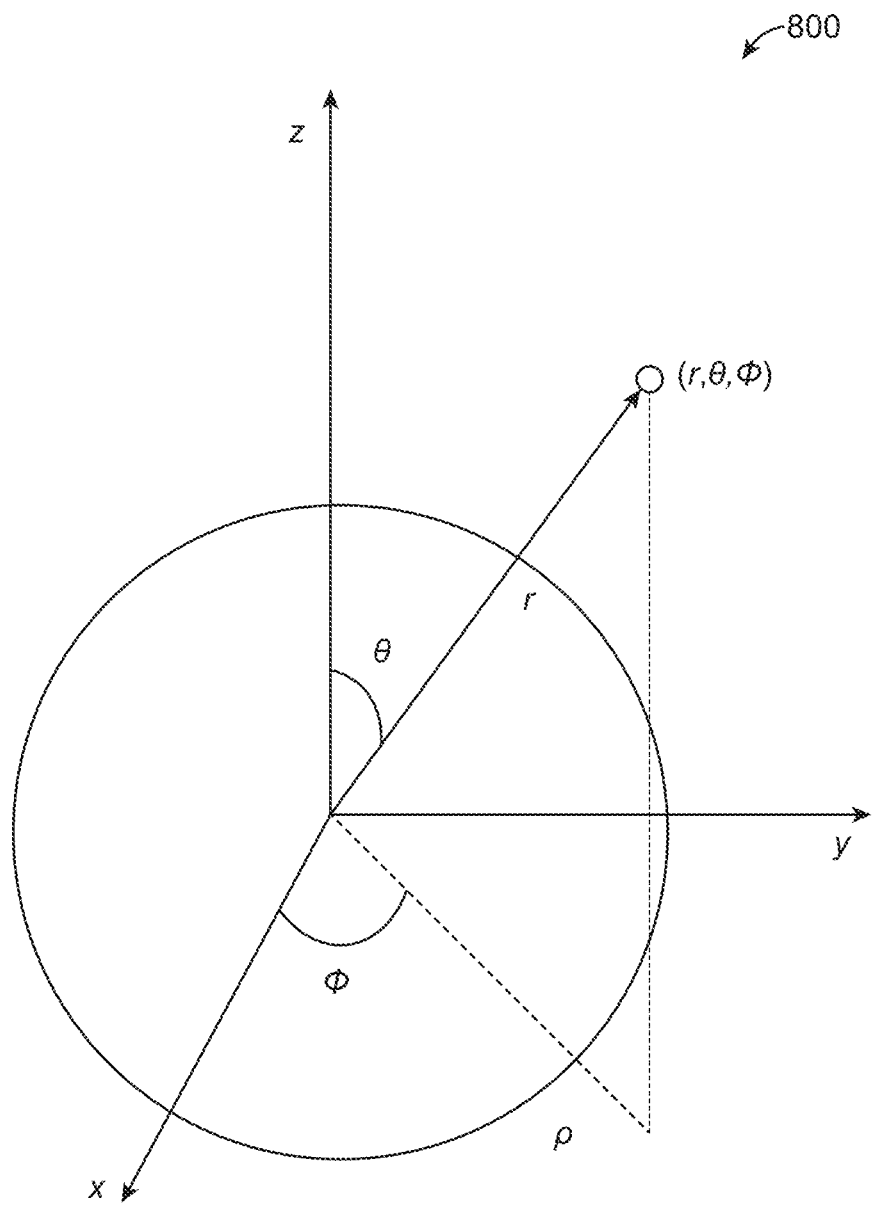
FIG. 8 illustrates a coordinate system used to describe the corneal position according to an embodiment.

In another embodiment, an example ray trace illustration for two different cornea radii are shown in FIG. 7. The two example corneal IOP pressures are 15 and 30 mmHG. As previously described, a series of multiple point sources 702 are arranged around the cornea. A front image sensor 704 and a side image sensor 712 are positioned to capture real image 706 and real image 710 respectively. In various embodiments, light from the multiple point sources 702 bounces of the cornea and the reflected light may be captured by the image sensors 704, 712. In the case of a low pressure cornea, the 15 mmHg cornea 716 has a lower y-axis projection, or a larger radius of curvature. The 30 mmHg cornea 708 has a higher y-axis projection and a smaller radius of curvature. The two cornea pressures may also cause the creation of two different virtual images, a 15 mmHg virtual image 714 and a 30 15 mmHg virtual image 714. The virtual cornea images may be formed below the surface of the cornea. The positions of the spots corresponding to the multiple point sources in the real images may be different for the two IOP values (15 and 30 mmHg), demonstrating the possibility of using such images to calculate IOP values for the eye.

An example coordinate system is shown in FIG. 7. The origin of the spherical coordinate system may be the center of vision for the eye, or an arbitrary position along the cornea or inside the eye. Note that in the various embodiments, the orientation of the x-Axis does not reduce generality.

Figure 9:
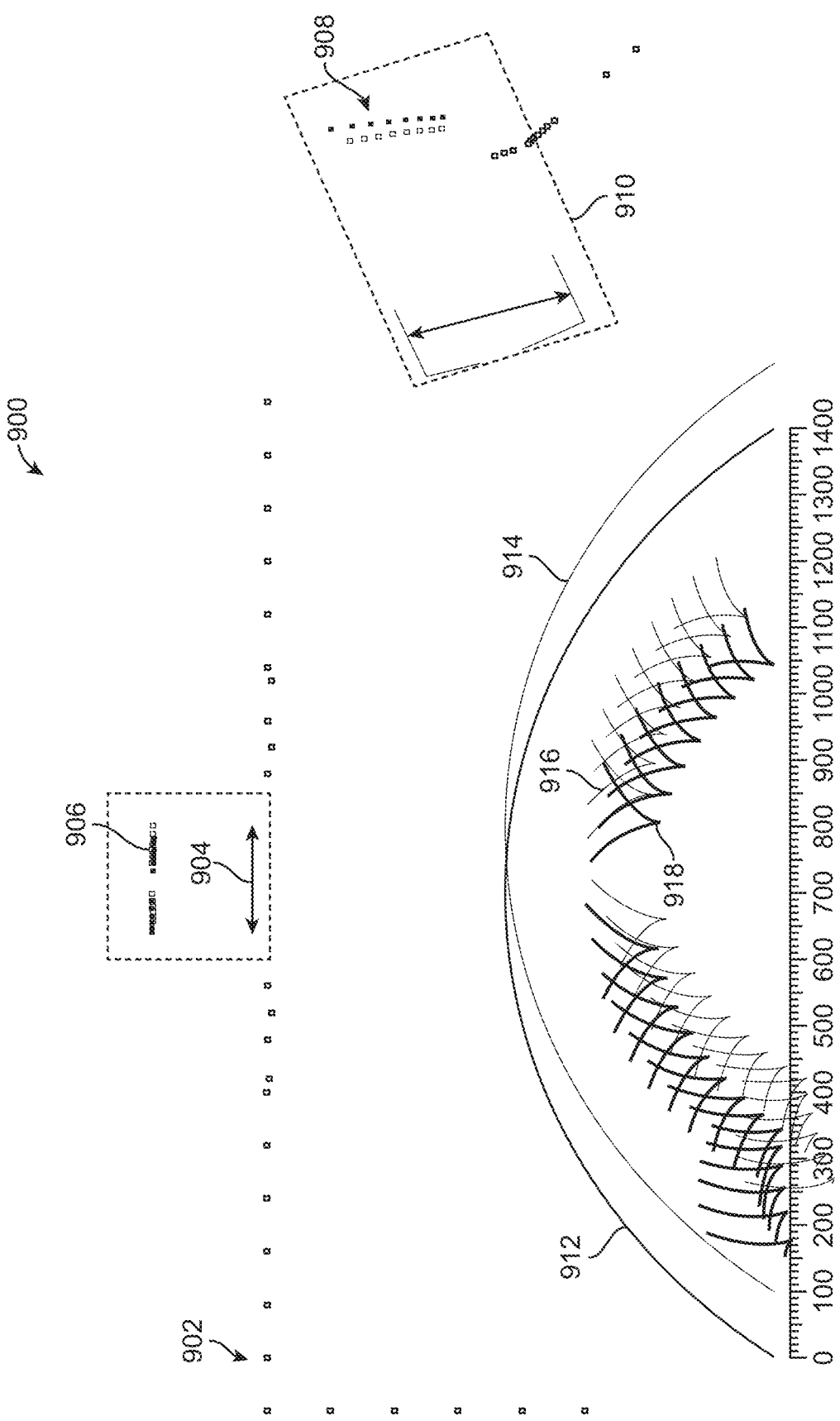
FIG. 9 illustrates a schematic ray trace showing corneal X-position changes according to an embodiment.

In an embodiment, the shifting of the cornea in a direction may be detected as shown in FIG. 9. In an embodiment, the multiple point sources 902 are arrayed around the cornea. A first image sensor 904 may capture a first real image 906, while a second image sensor 910 may capture a second real image 908. Second real image 908 may vary from one image to another based on the x-axis shift of the cornea over time. A left shift cornea 912 may be slightly shifted from the position of a right shift cornea 914, with corresponding left shift virtual image 918 and right shift virtual image 916 respectively. Using the shifted images between a first point in time T1 and a second point in time T2, the shift in the cornea may be imaged, and used to determine the shift in the X-position of the cornea. Image analysis may be used to correlate the image data to produce reliable x-shift information.

Figure 10:
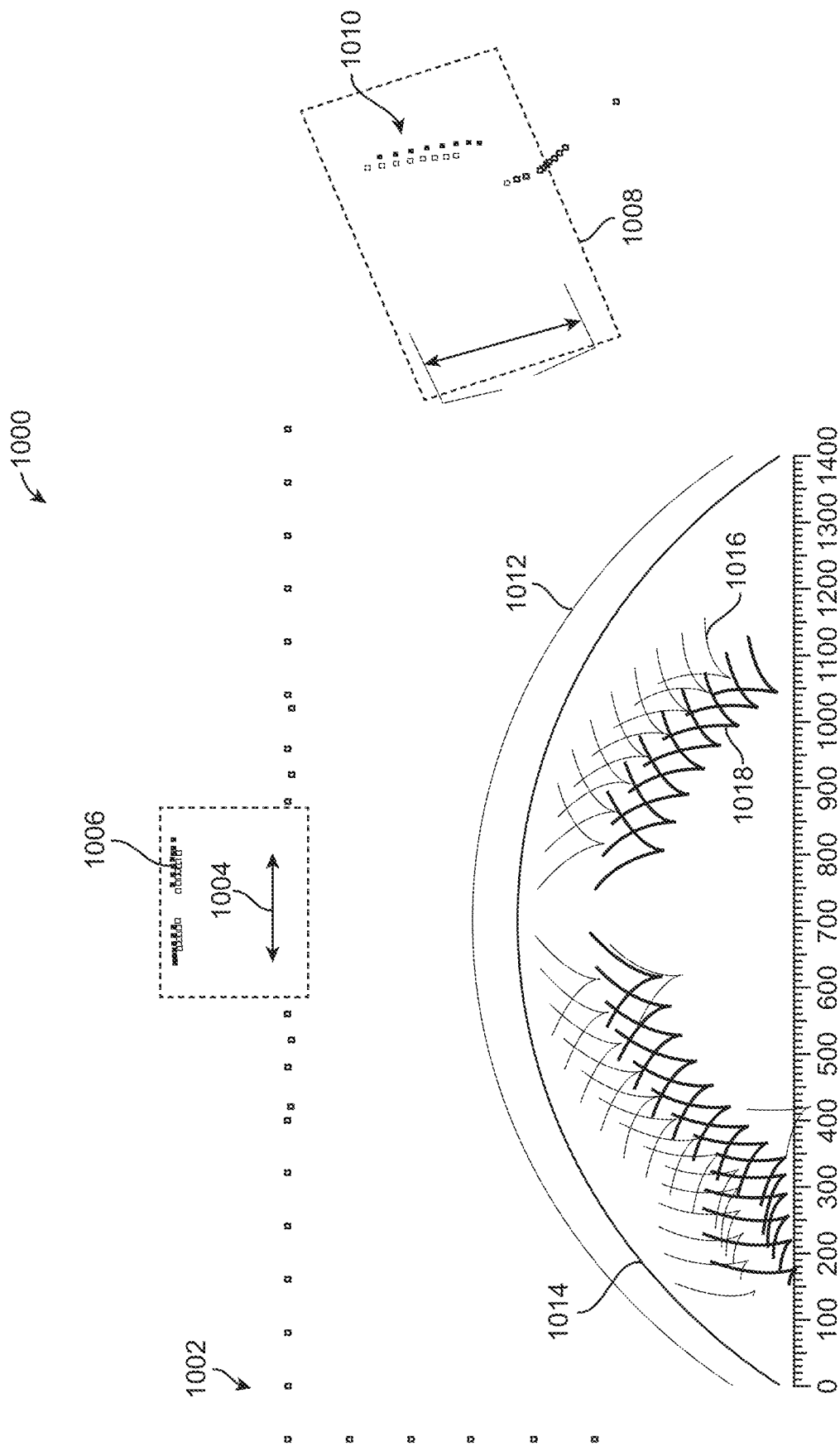
FIG. 10 illustrates a schematic ray trace showing corneal z-position changes according to an embodiment.

In another embodiment, the z position shift of the cornea may be determined as shown in a ray trace illustration as shown in FIG. 10. In an embodiment, multiple point sources 1002 produce light that reflects off the cornea. The reflected light may be captured by image sensor 1004 and side image sensor 1008. Real image 1006 and real image 1010 are collected from the image sensors. The cornea of the eye may shift in a z axis direction. In some embodiments, there may be z shift positive 1012 and a z shift negative 1014 corresponding to the movement of the cornea. Virtual images may be similarly adjusted, producing a positive virtual image 1016 that may correspond to the z shift positive 1012 and a negative virtual image 1018 that may correspond to the z shift negative 1014 cornea position. The positions of the spots in the real images 1006, 1010 represent different Z positions. The difference may be used to extract the Z position of the cornea through analysis of one or more of the various images.

Figure 11:
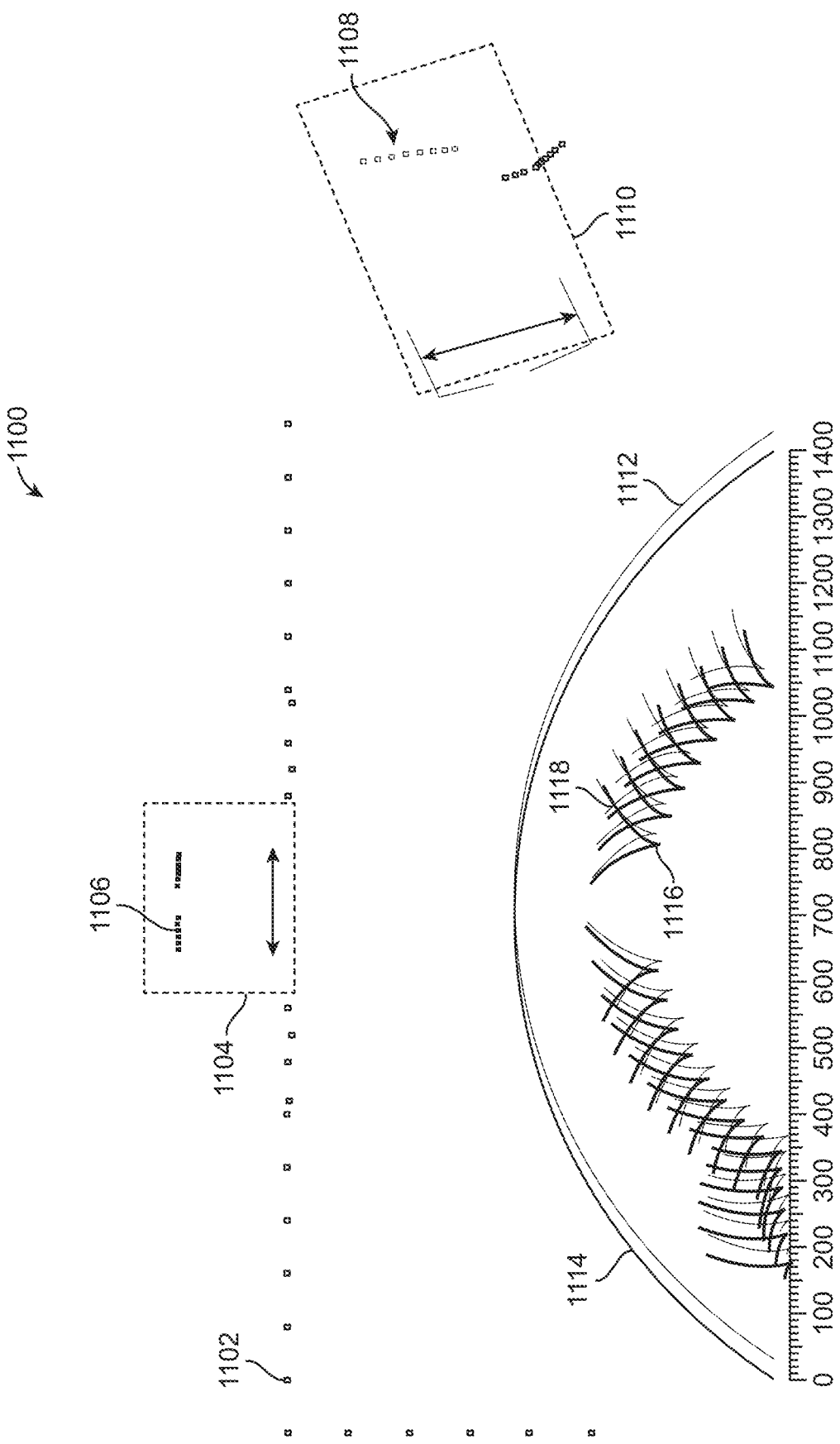
FIG. 11 illustrates a schematic ray trace showing image changes when the corneal angular position changes according to an embodiment.

In another embodiment, the angular (theta) shift can be determined using ray trace images as shown in FIG. 11. In an embodiment there may be multiple point sources 1102 of light. The light may reflect of the cornea and images may be captured in a front image sensor 1104 and side image sensor 1110, each producing real image 1106 and real image 1108 respectively. The cornea theta positive 1112 may represent a positive shift in the theta direction, while a cornea theta negative 1114 may represent a negative theta position shift. A positive virtual image 1116 and negative virtual image 1118 may also be detected. The positions of the spots in real images 1106, 1108 may represent two different theta tilt positions. The difference may be used to extract the angular tilt theta of the cornea through the analysis of the images 1106, 1108.

Figure 12:
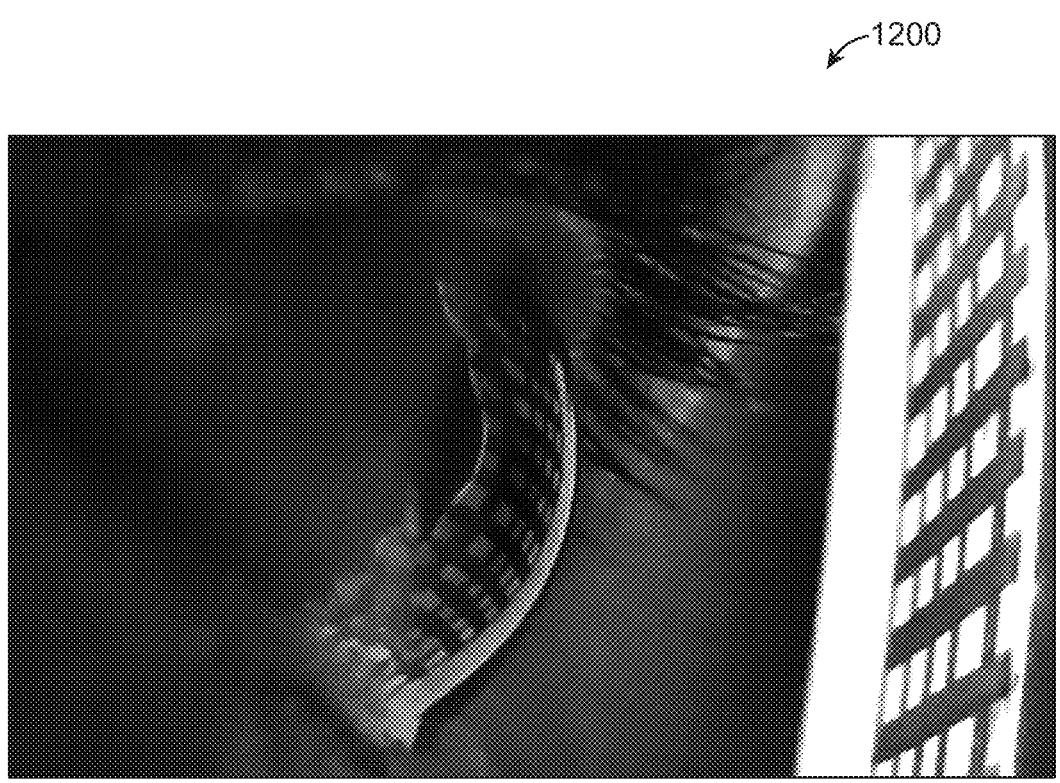
FIG. 12 illustrates a video frame capture according to an embodiment.

In an embodiment, a side view image of an eye may be seen, captured through a side facing image sensor (not shown), while the is illuminated using a matrix pattern from the front in FIG. 12.

Figure 13:
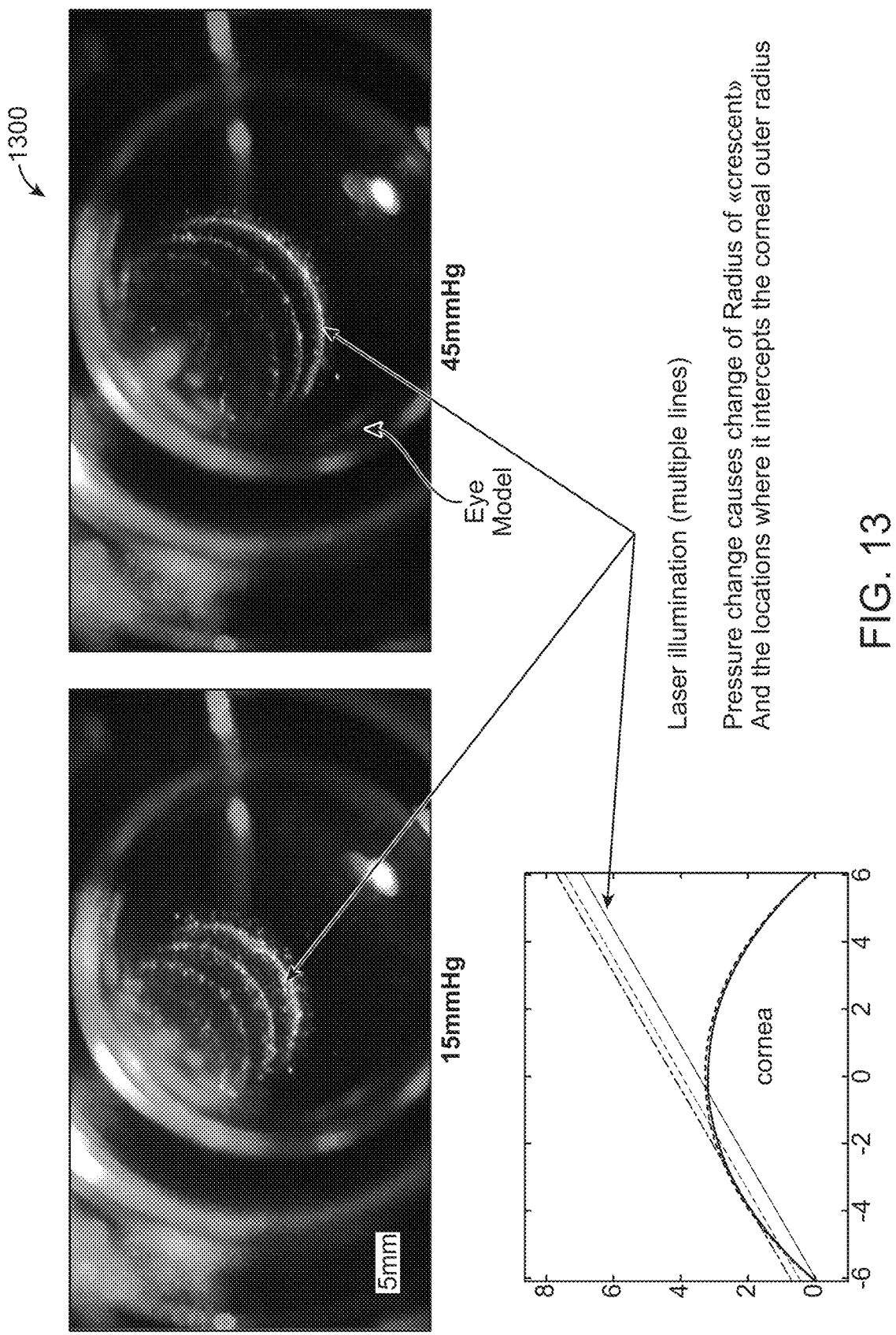
FIG. 13 illustrates an alternative video frame capture according to an embodiment.

In an embodiment, there is shown another example of illumination using laser energy formed into lines as shown in FIG. 13. In an embodiment, there may be shown a computation for laser lines incident on the cornea under two different pressure levels. It can be seen that the lines intercept the cornea at different positions for different IOP values. When the crescent shaped curve images are analyzed along with images of the point sources, the images contain enough information to accurately estimate the eye position with respect to the eyewear position, the corneal radius and the IOP.

Figure 14:
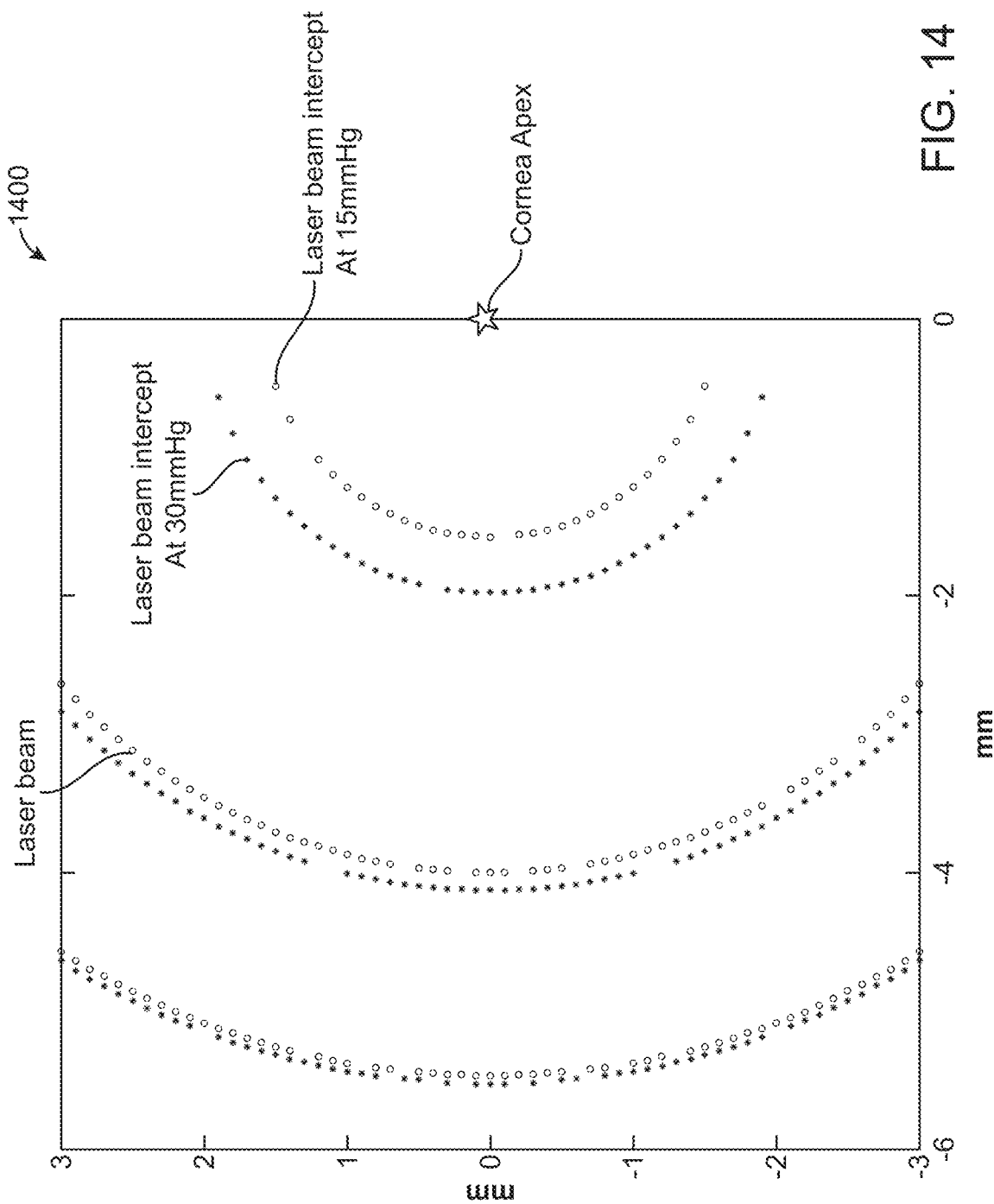
FIG. 14 illustrates a calculation showing changes in positions of laser points according to an embodiment.

In another embodiment, the intercept positions of a multitude of laser energy may be formed into spots by the hologram, and may be calculated for two different IOP values as shown in FIG. 14.

Figure 15:
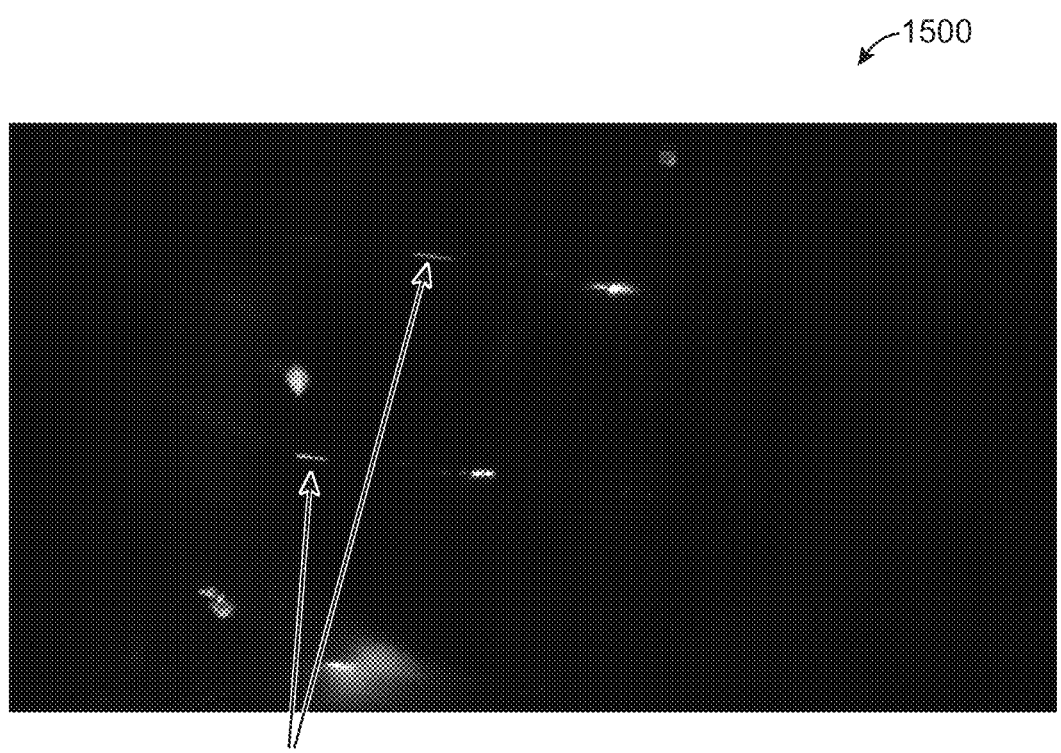
FIG. 15 illustrates a video frame capture according to an embodiment.

In another embodiment, a video frame capture from a front view camera (from inside the eyewear) with multiple laser energy spots as shown in FIG. 15. The reflection of the illuminating spots from the cornea, similar to the positions of spots previously described, may be visible by a front camera.

Figure 16:
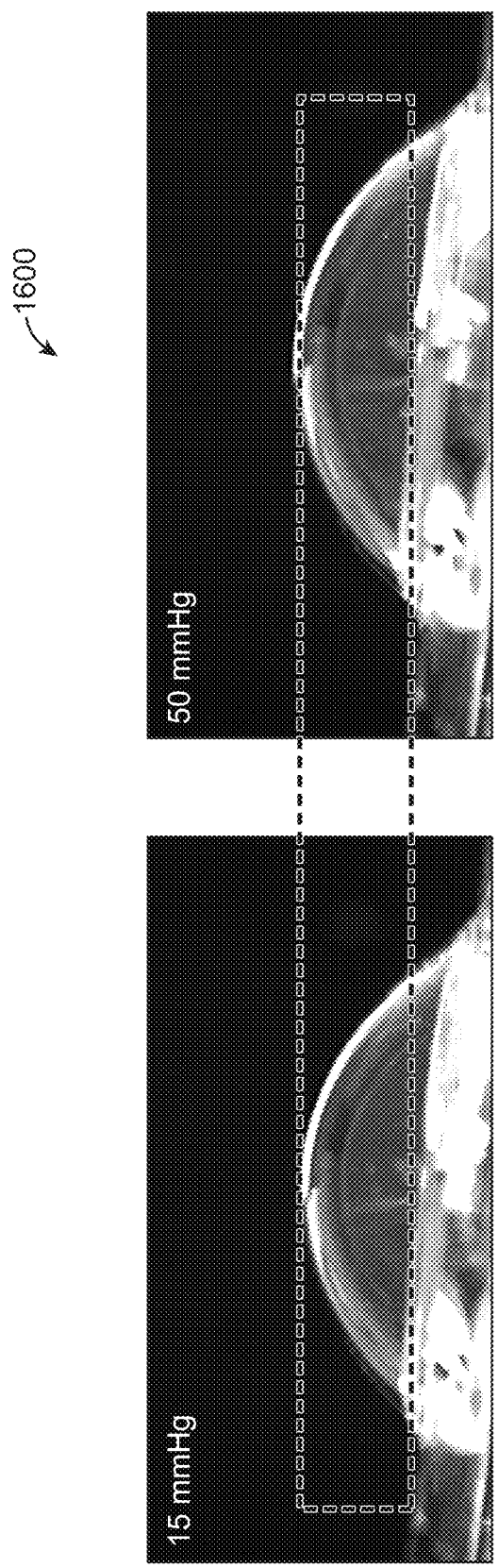
FIG. 16 illustrates example data extracted from video captures according to an embodiment.

In another embodiment, a side view of a model cornea under two different pressure settings may be seen in FIG. 16. The left figure represents the curvature and bulge of the cornea model when the model is exposed to 15 mmHg of fluid pressure. The right figure shows a slight increase in the bulge of the model when exposed to 50 mmHg pressure. The curvature of the model cornea may also be changing as the pressure increases or decreases. The curvature and bulge may be measured using the various techniques described herein.

Figure 17:
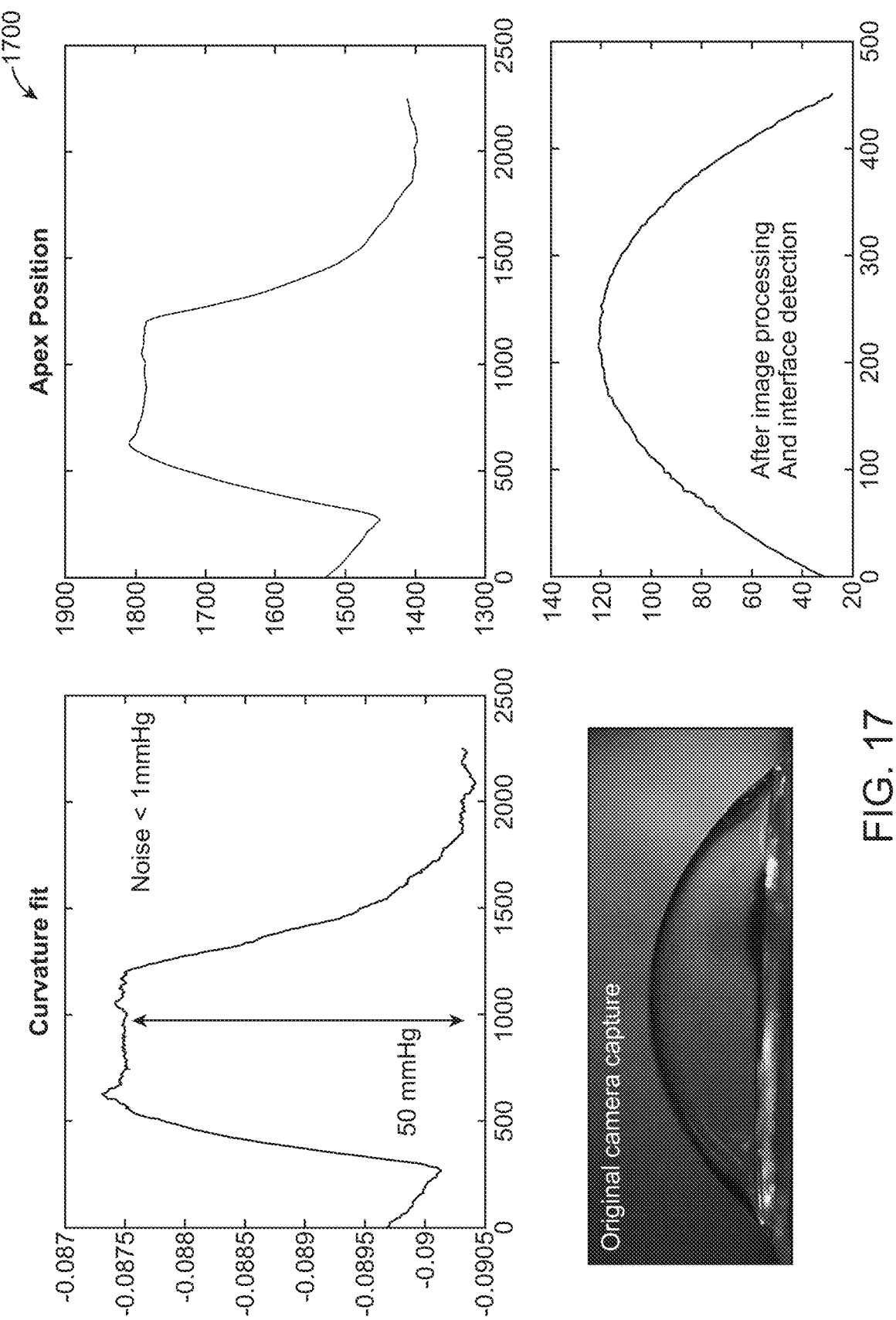
FIG. 17 illustrates a graph of data using a polynomial fit according to an embodiment.

In an embodiment, the curvature of the cornea may be captured in images, and quantified through analysis as shown in FIG. 17. The images may be processed to extract the interface between the cornea and air and to perform a polynomial fit to the extracted curves. The curvature and peak position may be separately extracted and plotted as shown in the top left and right plots. The changes in applied pressure may be accurately extracted from the fitted curves with a noise level below about 1 mmHg. In various embodiments, the fits may be high order polynomials—allowing baseline shifts due to linear positional shifts to be reduced or eliminated. In various embodiments, the image data from the image sensors on the eyewear may be input to a deep neural network that may be composed of image processing components, to reduce the image data to a set of data points. The image processing pipeline may contain trained feature extractors or matched-filtering, edge detection algorithms, filtering algorithms and/or other filters and algorithms. The use of several image sensors may allow determination of the position of the eye with respect to the illumination and eyewear image sensors as well as the head of the user. The algorithms may then be used with neural networks and conventional mathematical fitting methods to extract with high precision the curvature of the cornea.

Figure 18:
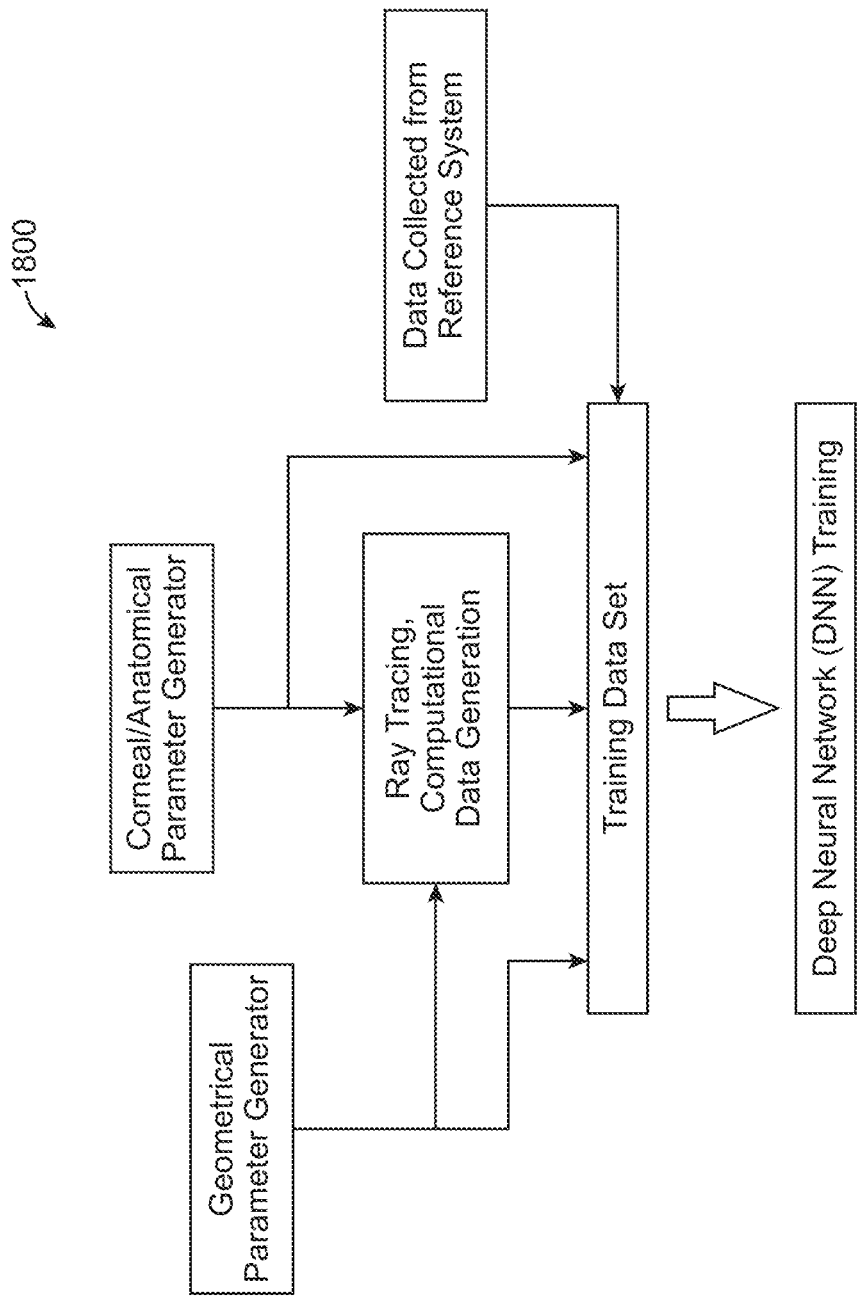
FIG. 18 illustrates a schematic of data processing according to an embodiment.

In an embodiment, there may be a method of training a neural network or deep neural network, as shown in FIG. 18. In an embodiment, the schematic diagram of the training method for the neural network/deep neural network (NN/DNN) may involve having the user undergo standard ophthalmologic measurements. These measurements may give accurate values for personal values of cornea thickness, position, and corneal topography in relation to a reference IOP level. The user may also undergo a brief data collection process where the eyewear may be used and reference data may be collected at the given IOP. In this fashion the eyewear may be calibrated to an individual user. All of this may be data collected from a reference system or systems. These measurements may personalize the system for a user with a unique personal corneal topography. The data collected from personalized measurements may then be fed, along with a computational model ("Geometrical Parameter generator" and "Cornel/Anatomical parameter generator"), into a ray tracing system to generate large amounts of image data for a wide variety of parameters. The outputs may then be used with the NN/DNN that contains an image processing pipeline to estimate corneal Radius and IOP.

In an embodiment, there may be an algorithm for the generation of training data sets for the training of a neural network, or a deep neural network, as shown in FIG. 19. The locations of spots in the real images from the various image sensors may be calculated for a variety of cornea positions and tilts, as well as cornea radii using ray tracing simulations. The locations of the spots and widths of the spots may be extracted from the ray tracing simulations and may form into vectors to be input into the neural network training software, and original cornea positions may be fed as desired outputs. The training procedure with a large data set may permit the neural network to handle this highly nonlinear problem to be solved with sufficient speed and accuracy. In an embodiment, the material shown in FIG. 19. May be considered as "pseudo-code" that summarizes the steps of data generation from ray-tracing simulations and formatting of the data to train the neural network.

Figure 20:
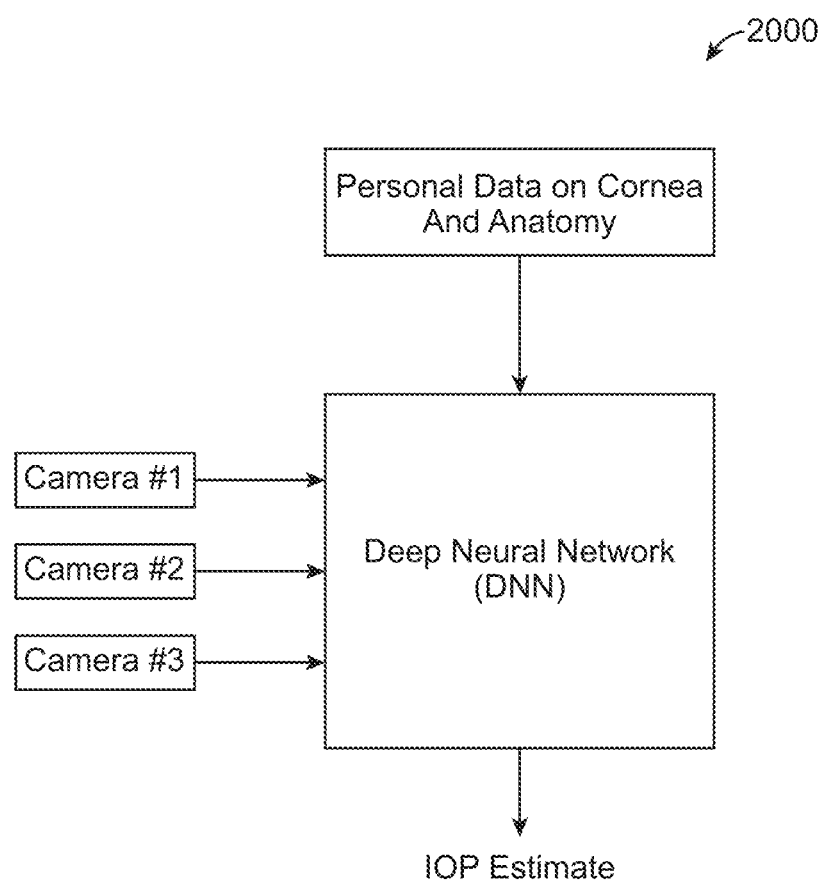
FIG. 20 illustrates a data processing flow chart according to an embodiment.

In an embodiment, the basic operation pipeline of the eyewear during measurement may be seen in FIG. 20. The eyewear may use image sensors, such as cameras, to capture images. The captured images may be combined with the personal ophthalmologic and anatomic data. The images may be fed into the deep neural network (DNN) with an image processing front-end, to achieve an IOP estimate. The IOP estimates may be updated at video rates, providing near real time output.

Figure 21:
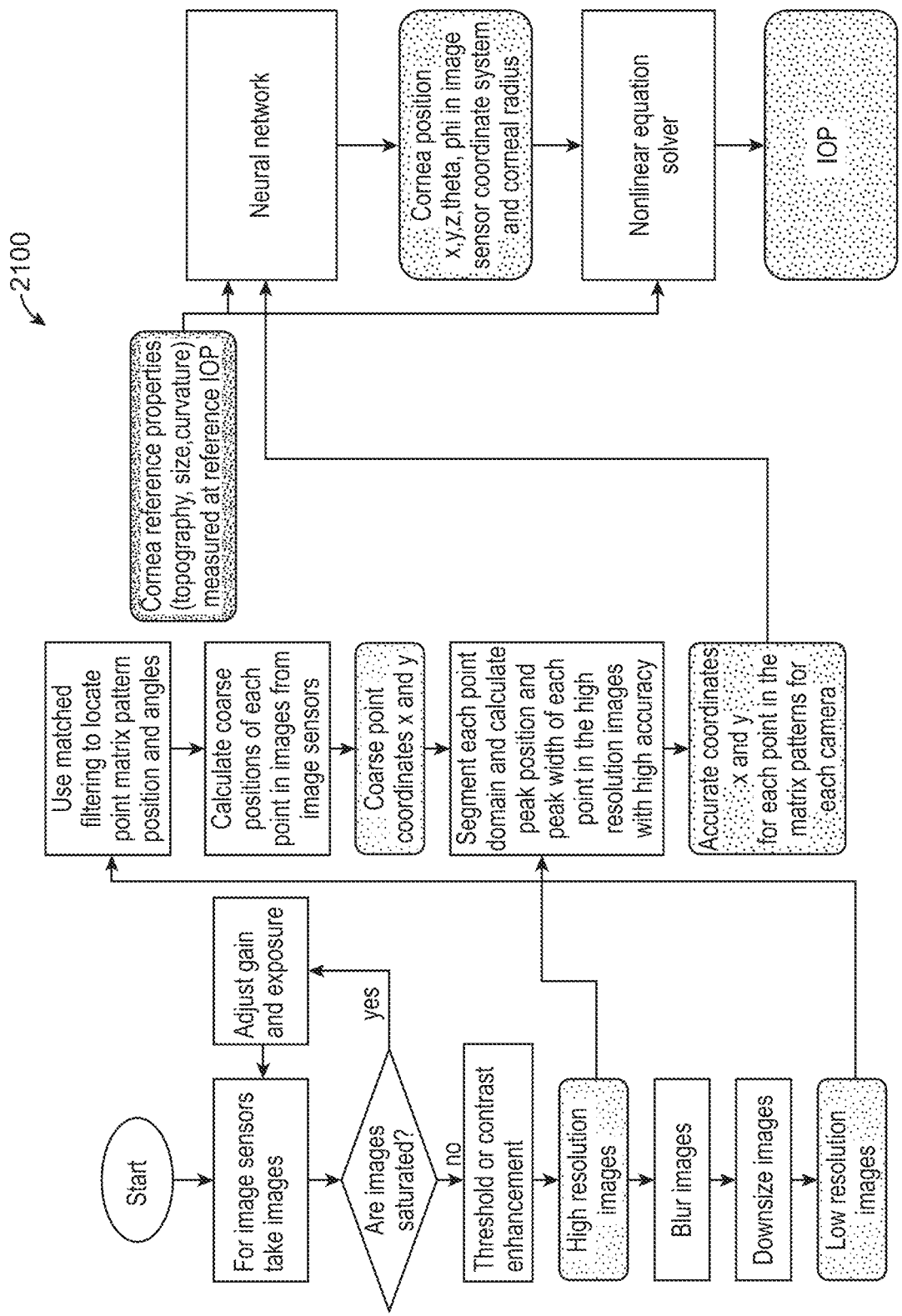
FIG. 21 illustrates an example data processing pipeline according to an embodiment.

In an embodiment, the pipeline for data processing may be seen in greater detail, as may be seen in FIG. 21. In an embodiment, the exposure level, gain, brightness and contrast settings of the image sensor may be adjusted rapidly to capture non-saturated images. In some embodiments this adjustment may be done for each light source, even if there may be multiple point sources as described herein. The images may be evaluated for image saturation, and if the image saturation is too high, the gain and exposure of the image sensor may be adjusted, and the image taken again. If the image saturation is acceptable, the images may be passed through a threshold filter, eliminating the non-relevant background signals. High resolution images may be stored in a temporary memory. The high resolution images may be used to create blurred and lower resolution images (which may be useful for faster processing). The low-resolution images may then be passed through a match-filter or feature detection filter to locate point matric pattern position and angles. This function may allow the filter to identify each pinpoint of light in the image and match that pinpoint of light to the corresponding multiple point sources of light in each of the real images. The process may then calculate the coarse positions of each point of light in the real images from the image sensors. The process may then produce the appropriate x and y coordinates for each real image. The coarse locations may then be used to segment each point domain and calculate peak position and peak width of each point in the high resolution real images with accuracy. The accurate coordinates of x and y positions for each point in the matrix pattern for each image sensor (camera), as well as width of peaks may then be produced. The coordinate data, along with the cornea reference properties may then be fed into the neural network or deep neural network. The cornea reference properties may include, by way of nonlimiting examples, the topography of the cornea, the size, the curvature, and any other measurement taken at the reference IOP). The results of the peak locations and widths, and/or the accurate measurements, may be used with the previously trained neural network/DNN to estimate cornea position x, y, x, theta and phi in image sensor coordinate system and corneal radius (radius of curvature). A nonlinear equation solver may be used to convert the radius of curvature into an IOP reading.

In another embodiment, the IOP reading may be used with a lookup table (not shown) to determine a dose of a drug. The drug dose may then be dispensed through the drug delivery device.

Figure 22:
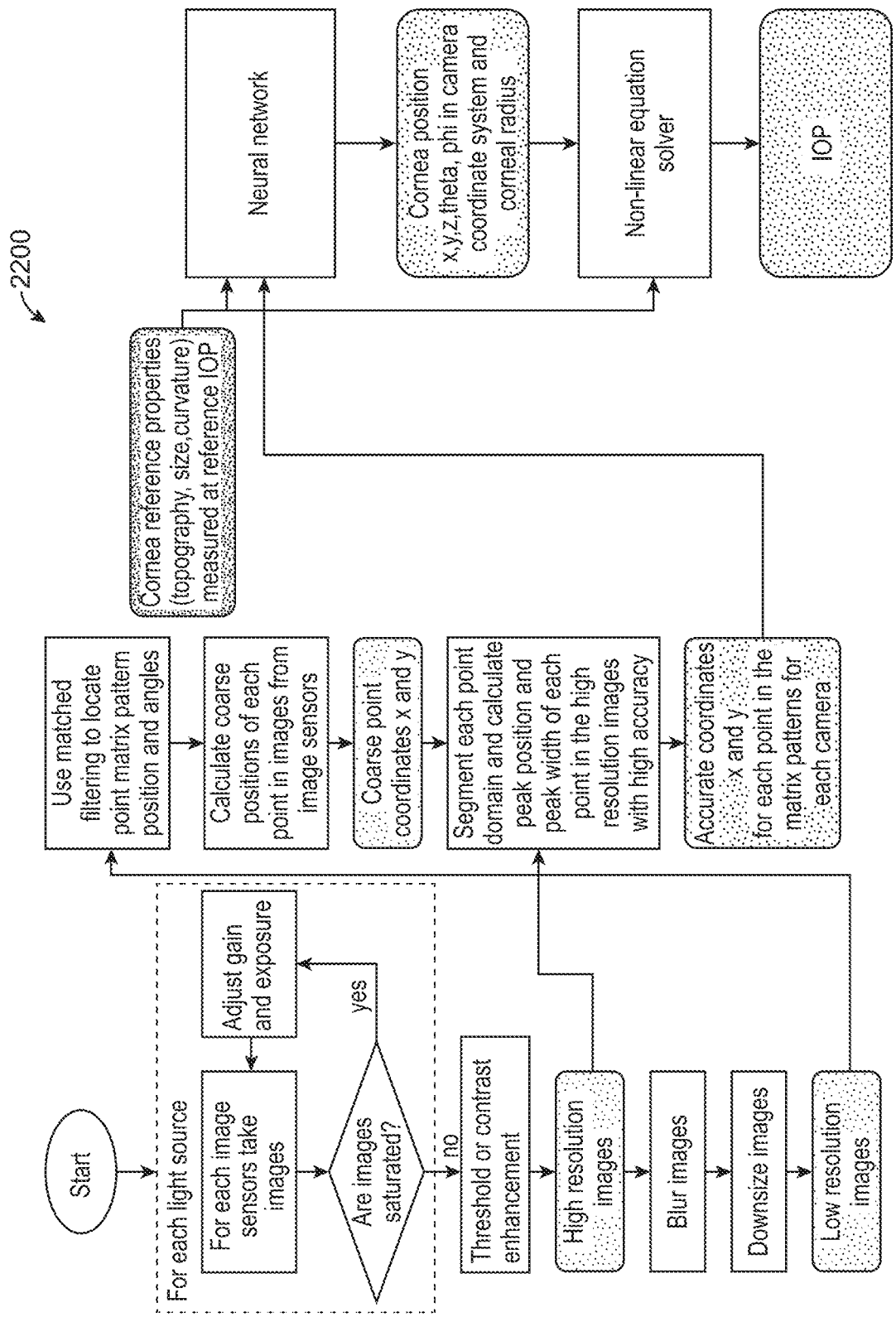
FIG. 22 illustrates another example data processing pipeline according to an embodiment.

In another embodiment, the pipeline for data processing may be adjusted to include a switching between different illumination sources at the beginning of the pipeline as shown in FIG. 22. The switching between different illumination sources may allow facile separation of image spots in the real images corresponding to different light sources, thereby speeding up the image processing, as well as improving accuracy of data collection.

In various embodiments, the virtual images generally may not be used themselves in the process. The real images may be formed from the virtual images after the image sensor focus light from the virtual images onto the imaging plane of the various image sensors.

The advantages of the present invention include, without limitation, a robust process for making of highly sensitive wearable contact lens sensors that have no electrical power or circuits and can be monitored remotely by a simple camera like one found in a mobile phone.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

What is claimed is:

1. An eyewear device for measuring intraocular pressure, the device comprising:
   a frame;
   a first lens mounted to the frame, wherein the lens is positioned in the frame so as to be in a user's normal viewing angle, wherein the lens does not obstruct a field of view of the user;
   an illumination source, the illumination source positioned to illuminate an eye of the user;
   an image sensor, the image sensor positioned to capture images of the eye of the user;
   a communication portal, the communication portal being in electronic communication with a computation device;
   a drug dispensing device, the drug dispensing device being aligned to deliver a dose of a drug to the eye of the user;
   wherein the illumination source, the image sensor, the communication portal and the drug dispensing device are mounted to the frame or to the lens.

2. The eyewear device of claim 1, wherein the first lens has a width to extend over the normal field of vision of a user who can see with two eyes.

3. The eyewear device of claim 1, wherein a second lens is mounted to the frame, the second lens positioned to be in the field of view of a second eye of the user.

4. The eyewear device of claim 1, wherein the communication portal comprises an antenna for wireless data transmission to a computational device.

5. The eyewear device of claim 4, wherein the computational device is a cellular phone, a tablet computer, or a laptop computer.

6. The eyewear device of claim 4, wherein the computational device is in a cloud based computer.

7. The eyewear device of claim 4, wherein the eyewear is a pair of goggles.

8. The eyewear device of claim 4, wherein the illumination source further comprises:
   a waveguide structure having a plurality of sparse outcouplers, the outcouplers acting as point sources of illumination.

9. The eyewear device of claim 4, wherein the image sensor further comprises:
   a polarizing filter, the polarizing filter allowing the camera to capture images using only illumination for the illumination source.

10. The eyewear device of claim 1, wherein the image sensor further comprises:
    a waveguide structure with at least one sparse outcoupler; and
    a polarizing filter.

11. The eyewear device of claim 10, wherein the waveguide structure acts as a point source of light while enabling see through vision of the eye of the user.

12. The eyewear device of claim 10, wherein the polarizing filter blocks the ambient light of one wavelength, allowing the image sensor with cross polarizers in its imaging path to capture only illumination from inside the eyewear.

13. The eyewear device of claim 1, further comprising an array of point sources of microscale dimensions, wherein the array of point sources is integrated with the lens to allow controlled and see-through illumination.

14. The eyewear device of claim 1, wherein the image sensor is a camera.

15. A method for training an image processing pipeline, the method comprising:
- collecting personalized ophthalmologic data on a user's anatomy and a user's corneal properties at a known IOP;
- collecting personalized data from an eyewear device for measuring IOP, wherein personalized data is collected without obstructing the user's field of vision; and
- using computational models and ray tracing under one or more geometric configurations to generate at least one set of training data for a neural network components pipeline.

16. A system for measuring and treating IOP, the system comprising:
- a computational device;
- a wearable eyewear device for collecting IOP data, the wearable eyewear device being in signal communication with the computational device, the wearable eyewear device having a drug dispensing component, the wearable eyewear not obstructing the field of view of a user;
- a database containing a user profile including personalized ophthalmologic reference data, the database being accessible by the computational device;
- a computer implemented program for training an image processing pipeline, the program producing an IOP data for accurate measuring of a user's IOP in at least one eye, wherein the computer implemented program resides on the computational device;
- wherein data from the database and the IOP data are used to determine a treatment regimen for a user's eye, and a treatment regimen is communicated to the eyewear device through signal communication, and the drug dispensing component dispenses a treatment drug according to the treatment regimen.

17. The system of claim 16, wherein the computational device is a cell phone, tablet computer or laptop computer.

\* \* \* \* \*